United States Patent
Brown et al.

(10) Patent No.: US 12,128,118 B2
(45) Date of Patent: Oct. 29, 2024

(54) AEROSOL DISPENSER CONTAINING A HAIRSPRAY COMPOSITION AND A NITROGEN PROPELLANT

(71) Applicant: The Procter & Gamble Company, Cincinnati, OH (US)

(72) Inventors: Jodi Lee Brown, Cincinnati, OH (US); Mikael Antonio Vicente, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 252 days.

(21) Appl. No.: 17/874,600

(22) Filed: Jul. 27, 2022

(65) Prior Publication Data

US 2023/0043188 A1    Feb. 9, 2023

Related U.S. Application Data

(60) Provisional application No. 63/226,959, filed on Jul. 29, 2021.

(51) Int. Cl.
| | |
|---|---|
| *A61K 8/04* | (2006.01) |
| *A45D 19/02* | (2006.01) |
| *A61K 8/19* | (2006.01) |
| *A61K 8/81* | (2006.01) |

(Continued)

(52) U.S. Cl.
CPC .............. *A61K 8/046* (2013.01); *A45D 19/02* (2013.01); *A61K 8/19* (2013.01); *A61K 8/8152* (2013.01); *A61K 8/817* (2013.01); *A61K 8/8176* (2013.01); *B05B 7/0483* (2013.01); *B65D 83/48* (2013.01);

(Continued)

(58) Field of Classification Search
CPC ........ A61K 8/046; A61K 8/19; A61K 8/8152; A61K 8/817; A61K 8/8176; A61K 2800/87; A45D 19/02; A45D 2200/057; B65D 83/48; B05B 7/0483
See application file for complete search history.

(56) References Cited

U.S. PATENT DOCUMENTS

| | | |
|---|---|---|
| 1,155,735 A | 10/1915 | Josse et al. |
| 1,324,579 A | 12/1919 | Binks |
| 1,367,769 A | 2/1921 | Coffey |

(Continued)

FOREIGN PATENT DOCUMENTS

| | | |
|---|---|---|
| CN | 101203271 A | 6/2008 |
| CN | 100544828 C | 9/2009 |

(Continued)

OTHER PUBLICATIONS

"Personal Care Polymers", Product Catalog, National Starch & Chemical, 2000, 16 pages.

(Continued)

*Primary Examiner* — Frederick C Nicolas
(74) *Attorney, Agent, or Firm* — John G. Powell; Alexandra S. Anoff

(57) ABSTRACT

An aerosol hairspray product with a spray device and a pressurizable container having a container wall which encloses a reservoir for storing a compressed gas propellant and a hairspray composition. The hairspray composition can be ethanol-based or ethanol-free. The spray properties of the product, including the spray rate and median droplet size, can be maintained throughout the lifetime of the container.

19 Claims, 6 Drawing Sheets

(51) Int. Cl.
*B05B 7/04* (2006.01)
*B65D 83/48* (2006.01)
(52) U.S. Cl.
CPC .... *A45D 2200/057* (2013.01); *A61K 2800/87* (2013.01)

(56) References Cited

U.S. PATENT DOCUMENTS

| | | |
|---|---|---|
| 2,098,136 A | 11/1937 | Walter |
| 2,503,481 A | 4/1950 | Hallinan |
| 2,657,836 A | 11/1953 | Alfred et al. |
| 2,878,065 A | 3/1959 | Watkins |
| 3,054,563 A | 9/1962 | Steinen |
| 3,120,348 A | 2/1964 | O'Donnell |
| 3,137,416 A | 6/1964 | Shepherd et al. |
| 3,146,922 A | 9/1964 | Tuttle, Jr. |
| 3,472,243 A | 10/1969 | Wall et al. |
| 3,472,604 A | 10/1969 | Dasher et al. |
| 3,475,114 A | 10/1969 | Bolinger et al. |
| 3,537,809 A | 11/1970 | Cednas et al. |
| 3,583,408 A | 6/1971 | Wall |
| 3,587,942 A | 6/1971 | Gailitis |
| 3,587,974 A | 6/1971 | Rosenkranz et al. |
| 3,619,114 A | 11/1971 | Anzuino et al. |
| 3,619,117 A | 11/1971 | Anzuino et al. |
| 3,619,118 A | 11/1971 | Anzuino et al. |
| 3,633,591 A | 1/1972 | Anzuino et al. |
| 3,634,022 A | 1/1972 | Robbins et al. |
| 3,661,161 A | 5/1972 | Kalopissis et al. |
| 3,676,550 A | 7/1972 | Anzuino |
| 3,678,157 A | 7/1972 | Kalopissis et al. |
| 3,680,738 A | 8/1972 | Vos et al. |
| 3,692,245 A | 9/1972 | Needham et al. |
| 3,819,090 A | 6/1974 | Birrell |
| 3,820,550 A | 6/1974 | Kinney et al. |
| 3,876,168 A | 4/1975 | Powers, Jr. |
| 3,882,114 A | 5/1975 | Kalopissis et al. |
| 3,909,195 A | 9/1975 | Machell et al. |
| 4,066,596 A | 1/1978 | Stern |
| 4,152,416 A | 5/1979 | Marra et al. |
| 4,167,692 A | 9/1979 | Sekiya et al. |
| 4,257,560 A | 3/1981 | Diamond |
| 4,260,110 A | 4/1981 | Werding |
| 4,278,659 A | 7/1981 | Breuer |
| 4,338,295 A | 7/1982 | Highley et al. |
| 4,384,679 A | 5/1983 | Sikora |
| 4,393,984 A | 7/1983 | Debard |
| 4,417,674 A | 11/1983 | Giuffredi |
| 4,487,369 A | 12/1984 | Du |
| 4,588,760 A | 5/1986 | Jachowicz et al. |
| 4,699,936 A | 10/1987 | Vasta |
| 4,719,104 A | 1/1988 | Patel |
| 4,726,945 A | 2/1988 | Patel et al. |
| 4,801,853 A | 1/1989 | Lewis et al. |
| 4,890,049 A | 12/1989 | Auinger |
| 4,925,101 A | 5/1990 | Konieczynski et al. |
| 5,002,761 A | 3/1991 | Mueller et al. |
| 5,067,655 A | 11/1991 | Farago et al. |
| 5,068,099 A | 11/1991 | Sramek |
| 5,068,587 A | 11/1991 | Nakamura et al. |
| 5,094,364 A | 3/1992 | Knickerbocker |
| 5,105,988 A | 4/1992 | Knickerbocker |
| 5,114,052 A | 5/1992 | Tiramani et al. |
| 5,126,124 A | 6/1992 | Tazi et al. |
| 5,160,729 A | 11/1992 | Login et al. |
| 5,182,098 A | 1/1993 | Kopolow et al. |
| 5,199,615 A | 4/1993 | Downing |
| 5,207,785 A | 5/1993 | Knickerbocker |
| 5,223,247 A | 6/1993 | Kopolow et al. |
| 5,234,166 A | 8/1993 | Foster et al. |
| 5,304,368 A | 4/1994 | Shernov et al. |
| 5,306,972 A | 4/1994 | Hokanson et al. |
| 5,335,858 A | 8/1994 | Dunning et al. |
| 5,348,731 A | 9/1994 | Patti et al. |
| 5,362,486 A | 11/1994 | Nandagiri et al. |
| 5,385,303 A | 1/1995 | Gosselin et al. |
| 5,411,185 A | 5/1995 | Drobish |
| 5,413,775 A | 5/1995 | Hatfield et al. |
| 5,441,728 A | 8/1995 | Tsaur et al. |
| 5,458,871 A | 10/1995 | Malawer et al. |
| 5,462,727 A | 10/1995 | Engler |
| 5,468,791 A | 11/1995 | Yuan |
| 5,525,657 A | 6/1996 | Anchor et al. |
| 5,526,985 A | 6/1996 | Martin |
| 5,540,389 A | 7/1996 | Knickerbocker |
| 5,560,544 A | 10/1996 | Merritt et al. |
| 5,614,799 A | 3/1997 | Anderson et al. |
| 5,637,296 A | 6/1997 | Rocafort |
| 5,665,804 A | 9/1997 | Hill et al. |
| 5,676,311 A | 10/1997 | Hartman |
| RE35,744 E | 3/1998 | Foster et al. |
| 5,735,465 A | 4/1998 | Laforcade |
| 5,752,396 A | 5/1998 | Schmid et al. |
| 5,901,907 A | 5/1999 | Hildebrandt |
| 5,912,522 A | 6/1999 | Rivera |
| 5,918,774 A | 7/1999 | Lund et al. |
| 5,927,604 A | 7/1999 | Laidler |
| 5,939,058 A | 8/1999 | Schwartz |
| 6,000,633 A | 12/1999 | Lund et al. |
| 6,009,868 A | 1/2000 | Nilson |
| 6,106,577 A | 8/2000 | Audousset et al. |
| 6,126,921 A | 10/2000 | Emmerling et al. |
| 6,136,884 A | 10/2000 | Chen et al. |
| 6,158,625 A | 12/2000 | Siegel et al. |
| 6,165,446 A | 12/2000 | Samain et al. |
| 6,199,766 B1 | 3/2001 | Fox |
| 6,215,261 B1 | 4/2001 | Becerra |
| 6,223,951 B1 | 5/2001 | Siegel et al. |
| 6,264,067 B1 | 7/2001 | Lasserre |
| 6,346,234 B1 | 2/2002 | Rollat et al. |
| 6,350,439 B1 | 2/2002 | Dupuis |
| 6,418,925 B1 | 7/2002 | Genova et al. |
| 6,440,404 B1 | 8/2002 | Dupuis |
| 6,482,808 B1 | 11/2002 | Springob et al. |
| 6,495,119 B1 | 12/2002 | Sturla et al. |
| 6,503,479 B1 | 1/2003 | Lesaulnier et al. |
| 6,509,012 B1 | 1/2003 | Hoessel et al. |
| 6,512,034 B1 | 1/2003 | Hamada et al. |
| 6,543,703 B2 | 4/2003 | Blake |
| 6,558,697 B2 | 5/2003 | Cannell et al. |
| 6,653,353 B2 | 11/2003 | Adams et al. |
| 6,655,552 B2 | 12/2003 | Aiken et al. |
| 6,727,668 B1 | 4/2004 | Maslov et al. |
| 6,740,317 B1 | 5/2004 | Cho et al. |
| 6,811,098 B2 | 11/2004 | Drechsel |
| 6,852,815 B1 | 2/2005 | Chuang et al. |
| 6,913,711 B2 | 7/2005 | Mckie et al. |
| 6,966,465 B2 | 11/2005 | Kang |
| 7,014,127 B2 | 3/2006 | Valpey, III et al. |
| 7,028,866 B2 | 4/2006 | Kunesh et al. |
| 7,102,307 B2 | 9/2006 | Shao |
| 7,169,380 B2 | 1/2007 | Rollat et al. |
| 7,205,271 B2 | 4/2007 | Drzewinski et al. |
| 7,240,860 B2 | 7/2007 | Griend |
| 7,240,862 B2 | 7/2007 | Grasselli et al. |
| 7,255,869 B2 | 8/2007 | Uchida et al. |
| 7,303,087 B2 | 12/2007 | Flashinski et al. |
| 7,364,055 B2 | 4/2008 | Yquel et al. |
| 7,423,082 B2 | 9/2008 | Lai |
| 7,448,517 B2 | 11/2008 | Shieh et al. |
| 7,452,525 B1 | 11/2008 | Berezkin et al. |
| 7,487,891 B2 | 2/2009 | Yerby et al. |
| 7,621,468 B2 | 11/2009 | Smith et al. |
| 7,888,904 B2 | 2/2011 | Mularcik |
| 7,926,741 B2 | 4/2011 | Laidler |
| 7,972,589 B2 | 7/2011 | Leighton et al. |
| 7,981,167 B2 | 7/2011 | Carballada et al. |
| 8,048,846 B2 | 11/2011 | Chahal et al. |
| 8,114,938 B2 | 2/2012 | Berezkin et al. |
| D658,009 S | 4/2012 | Davis et al. |
| 8,173,583 B2 | 5/2012 | Garcia et al. |
| 8,241,613 B2 | 8/2012 | Candau et al. |
| 8,318,879 B2 | 11/2012 | Hashemzadeh |
| 8,328,120 B2 | 12/2012 | Vanblaere et al. |

(56) References Cited

U.S. PATENT DOCUMENTS

| | | | |
|---|---|---|---|
| D681,344 S | 5/2013 | Davis et al. | |
| 8,440,211 B2 | 5/2013 | Auguste | |
| 8,752,737 B2 * | 6/2014 | Ghavami-Nasr | B65D 83/20 |
| | | | 222/402.1 |
| 8,981,696 B2 | 3/2015 | Bates et al. | |
| 9,174,229 B2 | 11/2015 | Smith | |
| 9,259,481 B2 | 2/2016 | Shin et al. | |
| 9,694,087 B2 | 7/2017 | Shin et al. | |
| 9,986,809 B2 * | 6/2018 | Brown | A61K 8/046 |
| 10,131,488 B2 | 11/2018 | Brown | |
| 10,426,979 B2 | 10/2019 | Birkel | |
| 2002/0028187 A1 | 3/2002 | Nekludoff et al. | |
| 2002/0085988 A1 | 7/2002 | Nambu | |
| 2002/0125462 A1 | 9/2002 | McKie et al. | |
| 2002/0150542 A1 | 10/2002 | Steinmetz et al. | |
| 2002/0176834 A1 | 11/2002 | Adams et al. | |
| 2003/0082223 A1 | 5/2003 | Healy et al. | |
| 2003/0103930 A1 | 6/2003 | Uchida et al. | |
| 2003/0106901 A1 | 6/2003 | Meshberg | |
| 2003/0175229 A1 | 9/2003 | Giroud | |
| 2003/0215399 A1 | 11/2003 | Smith et al. | |
| 2003/0215400 A1 | 11/2003 | Schroeder et al. | |
| 2004/0013615 A1 | 1/2004 | Dubief et al. | |
| 2004/0016062 A1 | 1/2004 | Plos | |
| 2004/0042974 A1 | 3/2004 | Dupuis | |
| 2004/0115151 A1 | 6/2004 | Giroud | |
| 2004/0136921 A1 | 7/2004 | Schulz et al. | |
| 2004/0144863 A1 | 7/2004 | Kendrick et al. | |
| 2004/0166071 A1 | 8/2004 | Pfaffernoschke et al. | |
| 2004/0245294 A1 | 12/2004 | Mineau et al. | |
| 2004/0261198 A1 | 12/2004 | Kainz et al. | |
| 2005/0023368 A1 | 2/2005 | Valpey, III et al. | |
| 2005/0052080 A1 | 3/2005 | Maslov et al. | |
| 2005/0063916 A1 | 3/2005 | Ishii et al. | |
| 2005/0137198 A1 | 6/2005 | Nelson | |
| 2005/0255067 A1 | 11/2005 | Leighton et al. | |
| 2006/0060554 A1 | 3/2006 | Garman | |
| 2006/0076171 A1 | 4/2006 | Donnelly et al. | |
| 2006/0105003 A9 | 5/2006 | Rollat-Corvol et al. | |
| 2007/0018017 A1 | 1/2007 | Tilton et al. | |
| 2007/0066506 A1 | 3/2007 | Behler et al. | |
| 2007/0241132 A1 | 10/2007 | Smith | |
| 2007/0245538 A1 | 10/2007 | Salameh | |
| 2007/0267447 A1 | 11/2007 | Kennedy | |
| 2007/0275020 A1 | 11/2007 | Lendlein et al. | |
| 2007/0277332 A1 | 12/2007 | Bimczok et al. | |
| 2007/0286833 A1 | 12/2007 | Keller et al. | |
| 2007/0292641 A1 | 12/2007 | Altonen et al. | |
| 2008/0003387 A1 | 1/2008 | Altonen et al. | |
| 2008/0008781 A1 | 1/2008 | Sweeney | |
| 2008/0017666 A1 | 1/2008 | Vanblaere et al. | |
| 2008/0020004 A1 | 1/2008 | Birkel et al. | |
| 2008/0035638 A1 | 2/2008 | Burghaus et al. | |
| 2008/0041884 A1 | 2/2008 | Chevalier | |
| 2008/0102051 A1 | 5/2008 | Huynh et al. | |
| 2008/0112898 A1 | 5/2008 | Schiemann et al. | |
| 2008/0116759 A1 | 5/2008 | Lin | |
| 2008/0152610 A1 | 6/2008 | Cajan et al. | |
| 2008/0166305 A1 | 7/2008 | Singh et al. | |
| 2008/0187505 A1 | 8/2008 | Speckbacher et al. | |
| 2008/0187506 A1 | 8/2008 | Carballada et al. | |
| 2008/0197152 A1 | 8/2008 | Neuhaus et al. | |
| 2008/0210253 A1 | 9/2008 | Carballada et al. | |
| 2008/0219934 A1 | 9/2008 | Kim et al. | |
| 2008/0279804 A1 | 11/2008 | Parker et al. | |
| 2008/0311050 A1 | 12/2008 | Lendlein et al. | |
| 2009/0010865 A1 | 1/2009 | Kim et al. | |
| 2009/0022681 A1 | 1/2009 | Carballada et al. | |
| 2009/0041689 A1 | 2/2009 | Berezkin et al. | |
| 2009/0050599 A1 | 2/2009 | Martin et al. | |
| 2009/0050634 A1 | 2/2009 | Girardot et al. | |
| 2009/0050638 A1 | 2/2009 | Smith et al. | |
| 2009/0057447 A1 | 3/2009 | Lowry et al. | |
| 2009/0060858 A1 | 3/2009 | Schwarzwaelder et al. | |
| 2009/0060859 A1 | 3/2009 | Garcia et al. | |
| 2009/0074697 A1 | 3/2009 | Huynh | |
| 2009/0084870 A1 | 4/2009 | Smith et al. | |
| 2009/0084872 A1 | 4/2009 | Vanblaere et al. | |
| 2009/0104138 A1 | 4/2009 | Shimatani et al. | |
| 2009/0118044 A1 | 5/2009 | Kuo et al. | |
| 2009/0124961 A1 | 5/2009 | Harman | |
| 2009/0160392 A1 | 6/2009 | Mularcik | |
| 2009/0295315 A1 | 12/2009 | Tarnow et al. | |
| 2009/0297467 A1 | 12/2009 | Laurent et al. | |
| 2010/0028286 A1 | 2/2010 | Carballada et al. | |
| 2010/0048988 A1 | 2/2010 | Pastorelli | |
| 2010/0052584 A1 | 3/2010 | Bates et al. | |
| 2010/0116909 A1 | 5/2010 | Abduljalil | |
| 2010/0123426 A1 | 5/2010 | Nashiki et al. | |
| 2010/0135917 A1 | 6/2010 | Winter et al. | |
| 2010/0189664 A1 | 7/2010 | Castro et al. | |
| 2010/0219211 A1 | 9/2010 | Smith | |
| 2011/0027211 A1 | 2/2011 | Viala et al. | |
| 2011/0030328 A1 | 2/2011 | Xu et al. | |
| 2011/0031328 A1 | 2/2011 | Rundle et al. | |
| 2011/0064684 A1 | 3/2011 | Krause et al. | |
| 2011/0114759 A1 | 5/2011 | Schmitz | |
| 2011/0158928 A1 | 6/2011 | Mueller et al. | |
| 2011/0192415 A1 | 8/2011 | Verboom et al. | |
| 2011/0205662 A1 | 8/2011 | Bates et al. | |
| 2011/0241592 A1 | 10/2011 | Lin | |
| 2011/0248099 A1 | 10/2011 | Ghavami-nasr | |
| 2011/0303148 A1 | 12/2011 | Xie | |
| 2011/0303766 A1 | 12/2011 | Smith | |
| 2011/0303767 A1 | 12/2011 | Smith | |
| 2012/0031419 A1 | 2/2012 | Batt et al. | |
| 2012/0034173 A1 | 2/2012 | Batt et al. | |
| 2012/0111898 A1 | 5/2012 | Neuhaus | |
| 2012/0180807 A1 | 7/2012 | Flohr | |
| 2012/0183486 A1 | 7/2012 | Flohr et al. | |
| 2012/0263669 A1 | 10/2012 | Mueller | |
| 2013/0058882 A1 | 3/2013 | Flohr et al. | |
| 2013/0068243 A1 | 3/2013 | Birkel | |
| 2013/0068849 A1 | 3/2013 | Birkel et al. | |
| 2013/0340785 A1 | 12/2013 | Baum | |
| 2014/0070025 A1 | 3/2014 | Dalbo | |
| 2014/0199251 A1 | 7/2014 | Ashida | |
| 2015/0000687 A1 | 1/2015 | Brown et al. | |
| 2015/0004200 A1 | 1/2015 | Brown et al. | |
| 2015/0232260 A1 | 8/2015 | Dann et al. | |
| 2016/0175238 A1 | 6/2016 | Shin et al. | |
| 2016/0250120 A1 | 9/2016 | Knappe et al. | |
| 2016/0263009 A1 | 9/2016 | Saito et al. | |
| 2016/0303023 A1 | 10/2016 | Bevinakatti | |
| 2016/0346175 A1 | 12/2016 | Sasik et al. | |
| 2016/0347536 A1 | 12/2016 | Brown et al. | |
| 2018/0263355 A1 | 9/2018 | Brown | |
| 2019/0384880 A1 | 12/2019 | Birkel | |
| 2023/0271771 A1 * | 8/2023 | Albertz | B65D 83/48 |
| | | | 222/145.5 |

FOREIGN PATENT DOCUMENTS

| | | |
|---|---|---|
| CN | 101678371 A | 3/2010 |
| CN | 101808749 A | 8/2010 |
| CN | 103002859 A | 3/2013 |
| CN | 103002860 A | 3/2013 |
| DE | 1935991 U | 3/1966 |
| DE | 2961896 | 3/1982 |
| DE | 3048011 A | 7/1982 |
| DE | 4121834 A1 | 1/1993 |
| DE | 4431577 A1 | 3/1996 |
| DE | 29615896 U1 | 1/1998 |
| DE | 29707765 U1 | 9/1998 |
| DE | 10259199 A1 | 6/2004 |
| DE | 102004036004 A1 | 2/2006 |
| DE | 102005018205 A1 | 10/2006 |
| DE | 102008024650 A1 | 4/2010 |
| EP | 0151973 A2 | 8/1985 |
| EP | 0379627 A1 | 8/1990 |
| EP | 0574607 A1 | 12/1993 |
| EP | 0471054 B1 | 5/1994 |
| EP | 0688577 A1 | 12/1995 |
| EP | 0644750 B1 | 4/1996 |

(56) References Cited

FOREIGN PATENT DOCUMENTS

| | | |
|---|---|---|
| EP | 0758545 B2 | 2/1997 |
| EP | 0618793 B1 | 5/1997 |
| EP | 0801990 A1 | 10/1997 |
| EP | 0696545 B1 | 6/1999 |
| EP | 1026220 A1 | 8/2000 |
| EP | 0873946 B1 | 7/2001 |
| EP | 0758222 B1 | 8/2001 |
| EP | 0791351 B1 | 12/2002 |
| EP | 1220956 B1 | 7/2003 |
| EP | 0832639 B1 | 1/2004 |
| EP | 1161934 B1 | 4/2004 |
| EP | 1092650 B1 | 12/2005 |
| EP | 1160178 B1 | 7/2006 |
| EP | 1681078 B1 | 12/2008 |
| EP | 1719500 B1 | 6/2010 |
| EP | 2407145 A1 | 1/2012 |
| EP | 2228319 B1 | 5/2013 |
| FR | 2784081 B1 | 4/2000 |
| GB | 2293336 A | 3/1996 |
| JP | S577728 A | 1/1982 |
| JP | H02262003 A | 10/1990 |
| JP | H0454116 A | 2/1992 |
| JP | H04208214 A | 7/1992 |
| JP | H06287115 A | 10/1994 |
| JP | H076881 A | 1/1995 |
| JP | 08301735 A | 11/1996 |
| JP | 09110630 A | 4/1997 |
| JP | H1073359 A | 3/1998 |
| JP | H10279436 A | 10/1998 |
| JP | 10337509 A | 12/1998 |
| JP | H11228398 A | 8/1999 |
| JP | H11513608 A | 11/1999 |
| JP | 2000109149 A | 4/2000 |
| JP | 2000343007 A | 12/2000 |
| JP | 2001227475 A | 8/2001 |
| JP | 2001302458 A | 10/2001 |
| JP | 2001521879 A | 11/2001 |
| JP | 2002029581 A | 1/2002 |
| JP | 2002503311 A | 1/2002 |
| JP | 2002511761 A | 4/2002 |
| JP | 2002284652 A | 10/2002 |
| JP | 2002540132 U | 11/2002 |
| JP | 2002347866 A | 12/2002 |
| JP | 2003054668 A | 2/2003 |
| JP | 2003521503 A | 7/2003 |
| JP | 2003230851 A | 8/2003 |
| JP | 2003336563 A | 11/2003 |
| JP | 2004002430 A | 1/2004 |
| JP | 2004195287 A | 7/2004 |
| JP | 3727112 B2 | 10/2005 |
| JP | 2006100419 A | 4/2006 |
| JP | 3828257 B2 | 7/2006 |
| JP | 2006213706 A | 8/2006 |
| JP | 2006517894 T | 8/2006 |
| JP | 2007117940 A | 5/2007 |
| JP | 3969517 B2 | 6/2007 |
| JP | 2007145878 A | 6/2007 |
| JP | 2007296428 A | 11/2007 |
| JP | 2008104929 A | 5/2008 |
| JP | 2008532858 A | 8/2008 |
| JP | 2008217645 A | 9/2008 |
| JP | 2008543938 A | 12/2008 |
| JP | 4278878 B2 | 3/2009 |
| JP | 2010540372 A | 12/2010 |
| JP | 2011092345 A | 5/2011 |
| JP | 2011190195 A | 9/2011 |
| JP | 5109311 B2 | 10/2012 |
| JP | 5207034 B2 | 3/2013 |
| JP | 5321122 B2 | 10/2013 |
| JP | 5883234 B2 | 3/2016 |
| JP | 6150912 B2 | 6/2017 |
| KR | 20080032055 A | 4/2008 |
| WO | 8905195 A1 | 6/1989 |
| WO | 9725259 A1 | 7/1997 |
| WO | 9729029 A1 | 8/1997 |
| WO | 9800354 A1 | 1/1998 |
| WO | 9829193 A1 | 7/1998 |
| WO | 9967216 A1 | 12/1999 |
| WO | 200045777 A1 | 8/2000 |
| WO | 200153157 A2 | 7/2001 |
| WO | 0170179 A1 | 9/2001 |
| WO | 200213773 A2 | 2/2002 |
| WO | 200245665 A1 | 6/2002 |
| WO | 03015929 A1 | 2/2003 |
| WO | 03061839 A1 | 7/2003 |
| WO | 2004043330 A2 | 5/2004 |
| WO | 2004062633 A1 | 7/2004 |
| WO | 2006073174 A1 | 7/2006 |
| WO | 2007062731 A1 | 6/2007 |
| WO | 2007099268 A2 | 9/2007 |
| WO | 2007099269 A2 | 9/2007 |
| WO | 2007099271 A2 | 9/2007 |
| WO | 2008104929 A1 | 9/2008 |
| WO | 2008148419 A1 | 12/2008 |
| WO | 2009030579 A1 | 3/2009 |
| WO | 2011056625 A1 | 5/2011 |
| WO | 2012009302 A1 | 1/2012 |
| WO | 2013040157 A1 | 3/2013 |
| WO | 2013040171 A2 | 3/2013 |
| WO | 2014210305 A2 | 12/2014 |
| WO | 2014210309 A2 | 12/2014 |

OTHER PUBLICATIONS

All office actions; U.S. Appl. No. 13/614,249, filed Sep. 13, 2012.
All office actions; U.S. Appl. No. 13/614,925, filed Sep. 13, 2012.
All office actions; U.S. Appl. No. 15/170,031, filed Jun. 1, 2016.
All office actions; U.S. Appl. No. 16/542,993, filed Aug. 16, 2019.
All office actions; U.S. Appl. No. 13/180,931; filed Jul. 12, 2011.
All office actions; U.S. Appl. No. 13/181,058; filed Jul. 12, 2011.
All office actions; U.S. Appl. No. 14/315,950, filed Jun. 26, 2014.
All Office Actions; U.S. Appl. No. 14/315,917, filed Jun. 26, 2014.
All Office Actions; U.S. Appl. No. 15/967,671, filed May 1, 2018.
All Office Actions; U.S. Appl. No. 12/814,253, filed Jun. 11, 2010.
All Office Actions; U.S. Appl. No. 12/814,248, filed Jun. 11, 2010.
All Office Actions; U.S. Appl. No. 13/614,205, filed Sep. 13, 2012.
All Office Actions; U.S. Appl. No. 14/939,090, filed Nov. 12, 2015.
Andrea Keenan; Hair Styling Formulations Containing Acudyne 180 Hair Fixative Polymer and Aculyn Rheology Modifiers; RD478088; Feb. 10, 2004, 6 pages.
CAS Registry entry for 1,2-difluoroethane, American Chemical Society, 2014, 6 pages.
CAS Registry entry for dimethyl ether, American Chemical Society, 2014, 6 pages.
Chadwick. Spray Technology & Marketing Dec. 2004. pg. 1-3. (Year: 2004).
Cook Philip M et al: "Low VOC hair—sprays . It depends very much on the choice of polymer", Aerosol Spray Report, Heidelberg, DE, vol. 37, No. 3, Jan. 1, 1998, pp. 20-23.
Miao Wang et al.; Acrylates/Hydroxyesters Acrylates Copolymer in Personal Care Applications: Acudyne DHR Durable Hold Resin; RD478006; Feb. 10, 2004, 16 pages.
Miao Wang; Mousse Formulations Containing Acudyne DHR or Acudyne 180 Hair Fixative Polymer and Aculyn 88 Rheology Modifier; RD510027; Oct. 10, 2006, 5 pages.
Rance. Journal of the Society of Cosmetic Chemists, vol. 23, No. 4, 197-208 (Year: 1972).
Troy, Remington: The Science and Practice of Pharmacy Baltimore: Lipponcott Williams & Wilkins, 2006, p. 1009 (Year: 2006).
"The Shellac Story- Shellac Properties", retrieved from the internet: http://www.shellac.in.shellac_properties.html, retrieved on Jul. 11, 2016, 1 page.

* cited by examiner

AEROSOL DISPENSER CONTAINING A HAIRSPRAY COMPOSITION AND A NITROGEN PROPELLANT

FIELD

An aerosol hairspray product with an aerosol spray device comprising a pressurize container that encloses a reservoir for storing a hairspray composition and a compressed gas propellant.

BACKGROUND

Hairstyling products such as hairsprays can be used to keep hair in place, protect hair from humidity, create volume, and can even keep flyaways at bay. Hairsprays are commonly packaged in an aerosol container, which is under pressure and includes a release valve that is used to emit the pressurized hairspray into the air as a fine mist propelled by a gas propellant. Typically, the propellant is a liquified hydrocarbon propellant. An advantage of a hydrocarbon propellant is that inside the container there is enough pressure to turn the gas into a liquid. As the hairspray product is dispensed, the product level inside the container drops, and more propellant evaporates into the headspace above the product, maintaining an approximately constant pressure, which in turn yields consistent spray properties, such as spray rate and average particle size distribution.

Even though hydrocarbon propellants provide substantial benefits, some consumers would prefer a hairspray product in an aerosol dispenser with a non-hydrocarbon propellant, such as compressed gases, which can include, but are not limited to, compressed air, nitrogen, inert gases, and carbon dioxide. Nitrogen can be especially desirable because it is non-toxic, non-flammable, relatively low in cost and generally inert.

However, it can be difficult to make a consumer acceptable aerosol hairspray product that uses a nitrogen propellant because, unlike liquified hydrocarbons, the nitrogen propellant is always in the vapor state and therefore the pressure in the container is reduced as product is dispensed, making it difficult to dispense the hairspray composition at a consumer acceptable particle size distribution and spray rate over the life of the container. As the pressure inside the container drops, the average particle size distribution increases, eventually releasing globs of hairspray that take too long to dry and can make the hair look dull, limp, and stiff. Eventually, the pressure can be so low that no product is released at all, even if there is product left in the can.

Therefore, there is a need for an aerosol dispenser that contains a hairspray product and a nitrogen gas propellant with consistent spray properties, such as spray rate and average particle size distribution for the life of the container.

SUMMARY

An aerosol hairspray product comprising: (a) a pressurizable container comprising a container wall which encloses a reservoir for storing a compressed gas propellant and a hairspray composition; wherein the hairspray composition comprises: (i) from about 60% to about 98.5% water, by weight of the hairspray composition; (ii) from about 1.5% to about 8% hairstyling polymer, by weight of the hairspray composition, wherein the hairstyling polymer is water-soluble; wherein the hairspray composition is substantially free of ethanol, isopropanol, and propanol; (b) a spraying device clinched onto the container for dispensing the hairspray composition from the reservoir of the container, wherein the spraying device comprises a valve assembly and a nozzle; wherein the valve assembly comprises: a housing with internal walls defining a valve chamber, the valve chamber having a liquid inlet for fluid communication with liquid in the aerosol spray device, and a gas inlet for fluid communication with gas in the aerosol spray device; and a valve stem having a proximal end and a distal end, the proximal end received in the valve chamber and the distal end projecting through a sealed opening in the valve chamber, the valve stem including an outlet flow conduit with an outlet aperture at the distal end and, more proximally, at least one first stem inlet for liquid and at least one second stem inlet for gas; wherein the housing includes a lip projecting inwardly from the internal walls around at least a perimeter of the valve stem to form a seal around the entire perimeter of the valve stem, wherein the valve chamber liquid inlet is proximal of the lip and the valve chamber gas inlet is distal of the lip; wherein the valve stem is moveable between: a closed position in which the at least one first stem inlet is distal of the lip and the at least one second stem inlet is distal of the sealed opening in the valve chamber, such that the at least one first stem inlet is not in fluid communication with the valve chamber liquid inlet and such that the at least one second stem inlet is not in fluid communication with the valve chamber gas inlet; and an open position in which the at least one first stem inlet is proximal of the lip so as to be in fluid communication with the valve chamber liquid inlet, and the at least one second stem inlet is proximal of the sealed opening in the valve chamber and at least partially distal of the lip so as to be in fluid communication with the valve chamber gas inlet, whereby a bubble laden flow is created in the outlet flow conduit.

An aerosol hairspray product comprising: (a) a pressurizable container comprising a container wall which encloses a reservoir for storing a compressed gas propellant and a hairspray composition; wherein the hairspray composition comprises: from about 60% to about 99% ethanol, by weight of the hairspray composition; from about 1.5% to about 8% hairstyling polymer, by weight of the hairspray composition, wherein the hairstyling polymer is alcohol-soluble; (b) a spraying device clinched onto the container for dispensing the hairspray composition from the reservoir of the container, wherein the spraying device comprises a valve assembly and a nozzle; wherein the valve assembly comprises: a housing with internal walls defining a valve chamber, the valve chamber having a liquid inlet for fluid communication with liquid in the aerosol spray device, and a gas inlet for fluid communication with gas in the aerosol spray device; and a valve stem having a proximal end and a distal end, the proximal end received in the valve chamber and the distal end projecting through a sealed opening in the valve chamber, the valve stem including an outlet flow conduit with an outlet aperture at the distal end and, more proximally, at least one first stem inlet for liquid and at least one second stem inlet for gas; wherein the housing includes a lip projecting inwardly from the internal walls around at least a perimeter of the valve stem to form a seal around the entire perimeter of the valve stem, wherein the valve chamber liquid inlet is proximal of the lip and the valve chamber gas inlet is distal of the lip; wherein the valve stem is moveable between: a closed position in which the at least one first stem inlet is distal of the lip and the at least one second stem inlet is distal of the sealed opening in the valve chamber, such that the at least one first stem inlet is not in fluid communication with the valve chamber liquid inlet and such that the at least one second stem inlet is not in fluid communication with the valve chamber gas inlet; and an open position in which the at least one first stem inlet is proximal of the lip so as to be in fluid communication with the valve chamber liquid inlet, and the at least one second stem inlet is proximal of the sealed opening in the valve chamber and at least partially distal of the lip so as to be in fluid communication with the valve chamber gas inlet, whereby a bubble laden flow is created in the outlet flow conduit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

While the specification concludes with claims particularly pointing out and distinctly claiming the subject matter of the present invention, it is believed that the invention can be more readily understood from the following description taken in connection with the accompanying drawings, in which:

DETAILED DESCRIPTION

Figure 1:
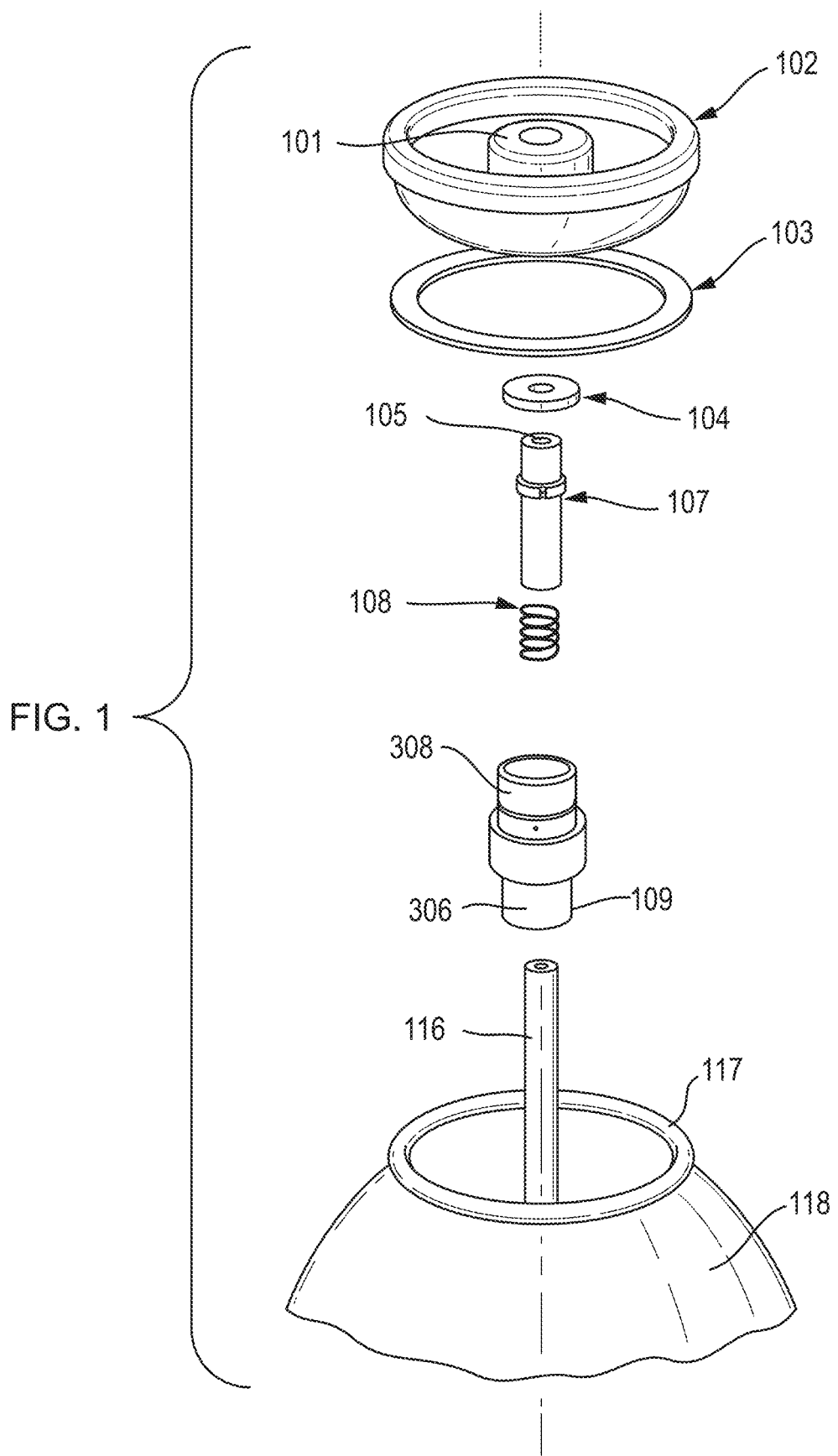
FIG. 1 shows an exploded diagram of an aerosol valve.

Many consumers would be interested in an aerosol hairspray product with a non-hydrocarbon propellant, such as compressed gas, that has excellent spray properties that are maintained throughout the life of the product (i.e. from 100% product (full can) to when 25% of the product was left in the can (end of can)). Compressed gas including air, nitrogen, carbon dioxide, and other inert gases can be desirable because they are non-toxic and non-flammable. In some examples, nitrogen gas can be preferred.

Hydrocarbon propellants are commonly used in aerosol hairspray products. These propellants are present (in the aerosol spray device) both a gas phase and a liquid phase, which is miscible with the liquid hairspray composition. Examples of hydrocarbon propellants can include butane, propane, dimethyl ether, isobutane, 1,1-Difluoroethane, or mixture thereof. On discharge, the gas phase propellant "propels" the liquid in container (including dissolved, liquid phase propellant through the nozzle).

One reason hydrocarbon propellants are popular is because they are capable of producing finer sprays than compressed gas aerosols because a large proportion of the liquefied gas "flash vaporizes" during discharge of liquid from the aerosol spray device and this rapid expansion gives rise to a fine spray. It is difficult to get these fine sprays using compressed air.

It was found that an aerosol hairspray product with an aerosol dispenser with a valve assembly, as described herein, in combination with ethanol-based and/or ethanol-free hairspray compositions and a compressed air propellant, such as nitrogen, can have consumer preferred spray properties (such as spray rate and particle size) throughout the life of the product.

Table 1, below, shows the desired spray properties for ethanol-based hairspray products and ethanol-free hairspray products.

TABLE 1

| | | Spray Properties |
|---|---|---|
| Ethanol-based Hairspray | Spray Rate | Ethanol-based hairspray products have a spray rate from about 0.3 to about 0.9 g/sec at both the initial spray/full can and when 25% of the hairspray composition remains in the container/end of can, according to the Delivery Rate Test Method, described hereafter. |
| | Dv50 Droplet Size | Ethanol-based hairspray products have a Dv50 droplet size is from about 40 μm to about 90 μm at both the initial spray/full can at when 25% of the composition remains in the can/end of can according to the Particle Size Distribution Test Method, described hereafter. |
| Ethanol-free Hairspray | Spray Rate | Ethanol-free hairspray products have a spray rate from about 0.3 to about 0.6 g/sec at both the initial spray/full can and when 25% of the hairspray composition remains in the container/end of can, according to the Delivery Rate Test Method, described hereafter. |
| | Dv50 Droplet Size | Ethanol-free hairspray products have a Dv50 droplet size is from about 40 μm to about 80 μm at both the initial spray/full can at when 25% of the composition remains in the can/end of can according to the Particle Size Distribution Test Method, described hereafter. |

The spray properties in Table 1 can be maintained (e.g. the spray rate will vary by no more than 10% and the Dv50 will vary by no more than 20 microns) between the initial/full can measurements and the measurement when 25% of the product remained in the container/end of can.

The spray rate and Dv50 droplet size deliver sufficient hairspray composition with film forming polymer to keep hair in place, provide long-lasting hold, create volume, and/or keep flyaways at bay, while having a non-sticky and natural hair look and feel. Since ethanol-free hairsprays can contain high levels of water (e.g. 30-60% water as a percentage by weight of the total amount of the composition ejected), instead of volatile ethanol, if too much hairspray is delivered the hair can become overwetted, which can take a long time to dry and can disrupt the internal ionic interactions of the hair allowing the hair to relax and lose the desired style. The dispensing problems can be exacerbated as propellant is expelled from the can throughout the lifetime of the product.

As used herein, "free of" refers to no detectable amount of the stated ingredient or thing.

As used herein, "substantially free of" refers to about 2% or less, alternatively 1% or less, alternatively 0.5% or less, and alternatively 0.1% or less of a stated ingredient.

"Hair," as used herein, means mammalian hair including scalp hair, facial hair and body hair, more preferably hair on the human head and scalp. "Hair shaft" means an individual hair strand and may be used interchangeably with the term "hair."

As used herein, the terms "include," "includes," and "including," are meant to be non-limiting and are understood to mean "comprise," "comprises," and "comprising," respectively. The term "water-soluble" as used herein refers to any material that is sufficiently soluble in water to form a single-phase solution to the naked eye at a concentration of 0.1% by weight of the material in water at 25° C. It may be necessary to adjust the pH of the mixture or fully neutralize the mixture after addition of the material to water to achieve the water solubility. These methods are well-known, for example, in the water-soluble hairstyling polymer applications industry and are typically instructed with the supplied material sample. Water-solubility is typically measured by the following protocol: 0.1% by weight of the material is added to distilled water at 25° C. and the pH adjusted/neutraliser added as needed. This is stirred vigorously on a magnetic stirrer set at 600 rpm, for 30 minutes. The solution is then allowed to settle for 1 hour and the number of phases observed by the naked eye. For example, where any solid material can be seen in an otherwise single-phase solution, then this is considered to be two phases.

The term "water-insoluble" as used herein refers to any material that is not "water-soluble". As used herein, "molecular weight" or "M.Wt." refers to the weight average molecular weight unless otherwise stated. Molecular weight is measured using industry standard method, gel permeation chromatography ("GPC").

In all embodiments of the present disclosure, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated.

Unless otherwise indicated, all measurements are understood to be made at about 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Spraying Device

The aerosol hairspray product comprises a pressurizable container. In some examples the container can be a can. The container or can may be formed from any suitable material including metal, plastic, pulp, glass, and combinations thereof. The pressure inside the reservoir can be measured with a pressure gauge (GCAS #60001439). The internal Nitrogen pressure can be determined based on the DOT 2Q regulations for an aerosol can. Therefore, the pressure inside the container can be from about from about 100 to about 159 PSIG, alternatively from about 110 to about 150 PSIG, alternatively from about 120 to about 140 PSIG, and alternatively about 130 PSIG, measured at 70° F.

Figure 2:
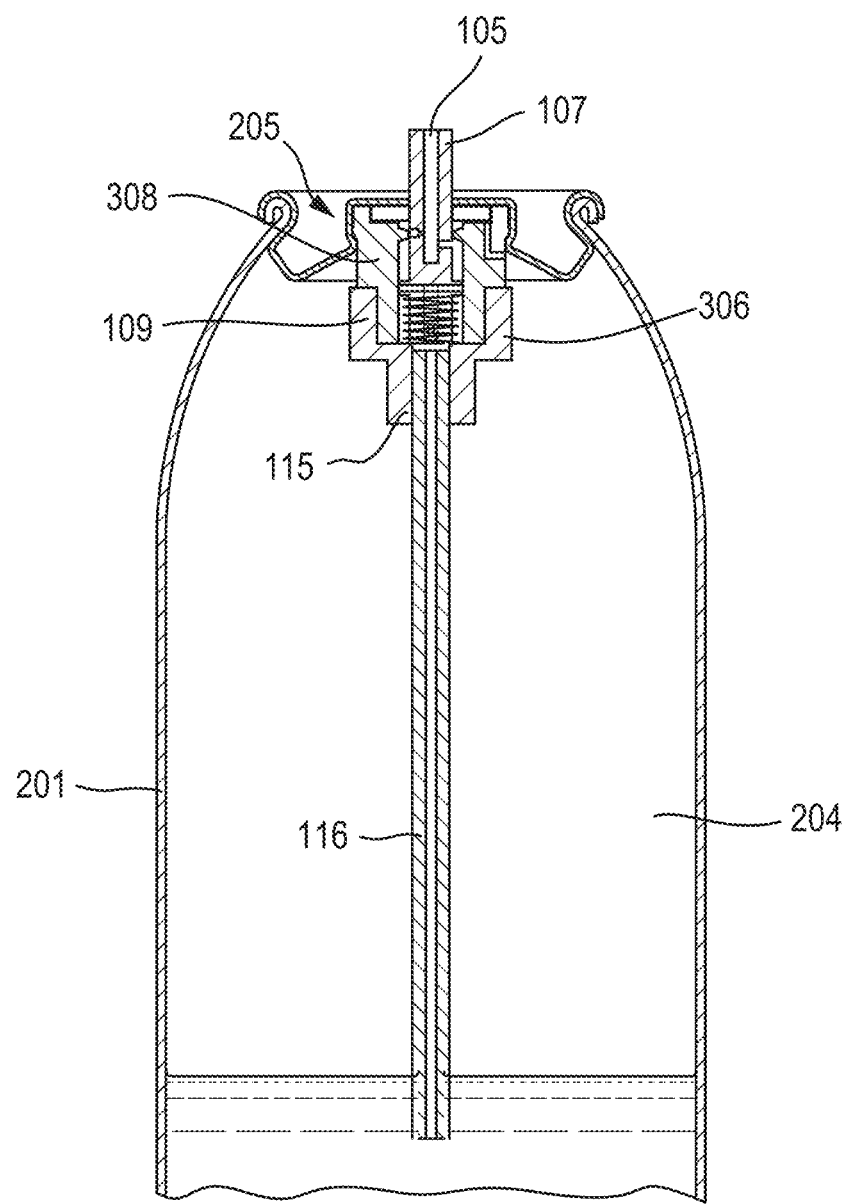
FIG. 2 shows the valve clinched on to the container.

FIG. 1 is an exploded view of the aerosol dispenser and FIG. 2 shows the valve clinched on to the can. The aerosol hairspray product comprises a spraying device attached to the container 118 for dispensing the hairspray composition from the reservoir 204 of the container 118, wherein the spraying device comprises a valve assembly 205 and a nozzle, wherein the valve assembly comprises a valve housing 109 a stem 107 and a spring means 108, and wherein the housing 109 comprises a lower cup portion 306 and an upper cap portion 308. The valve assembly 205 can be in liquid communication with the hairspray composition in the reservoir 204.

The valve housing 109 can have a valve tailpiece 115, and wherein the valve tailpiece 115 has an orifice, which receives a dip tube 116 that is capable of being in fluid communication with the hairspray in reservoir 204.

The valve tailpiece 115 orifice (which receives the dip tube 116) can have an inner diameter, wherein the inner diameter is from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm). The valve tailpiece 115 orifice has an inner diameter, wherein the inner diameter is from about 0.030 inch (0.762 mm) to about 0.070 inch (1.778 mm), or from about 0.035 inch (0.889 mm) to about 0.065 inch (1.651 mm), or from about 0.040 inch (1.016 mm) to about 0.060 inch (1.524 mm), or from about 0.045 inch (1.143 mm) to about 0.055 inch (1.397 mm), or from about 0.035 inch (0.889 mm) to about 0.045 inch (1.143 mm).

The stem 107 can have a stem orifice 105, which acts as an outlet for the contents of the container. The stem orifice 105 can have an inner diameter, wherein the inner diameter is from about 0.005 inch (0.127 mm) to about 0.025 inch (0.635 mm), or from about 0.008 inch (0.203 mm) to about 0.013 inch (0.340 mm), or from about 0.011 inch (0.279 mm) to about 0.014 inch (0.356 mm). The stem orifice 105 can have an inner diameter, wherein the inner diameter is from about 0.010 inch (0.254 mm) to about 0.020 inch (0.508 mm), or from about 0.015 inch (0.381 mm) to about 0.018 inch (0.457 mm).

The spring means 108 can be a spring 108.

The valve assembly 205 further comprises a stem gasket 104 that seals against the seat for the stem gasket on the stem 107 and thereby covers a side hole in the stem that leads to the stem orifice 105.

The stem 107 and valve housing 109 can be made of polyphenylene sulfone.

A valve suitable for use in the present invention is an Ecovalve® device provided by Salvalco, York, GB. Such a valve is disclosed in U.S. Pat. No. 10,071,849, which is incorporated herein by reference. In particular, col. 8, line 6 to col. 12, line 60 of U.S. Pat. No. 10,071,849, as well as FIGS. 4-7 therein, are incorporated herein by reference.

The stem gasket 104 is pre-assembled onto the stem 107 so that it seals against the seat for the stem gasket 106 on the stem 107 and covers a small side hole in the stem that leads to the stem orifice 105, which acts as an outlet for the contents of the container. A stainless-steel spring 108 is then prefitted to the base of the stem moulding. The mounting cup 102 is prefitted with a cup gasket 103 to form a gas-tight seal against the container curl 117 when the assembled valve is clinched to the container by standard industry means. The subassemblies described above are then crimped together using a standard pedestal crimping tool to make the fully assembled valve assembly 205. The stem gasket 104 is compressed by ~50% in thickness by the crimping procedure, and the pedestal of the mounting cup 102 is deformed during crimping to engage and retain a surface of valve housing 109. A polyethylene dip tube 116 is push-fitted into sealing engagement with the tailpiece 115 to complete the valve assembly. The container 118 is part-filled with hairspray composition inside the container 118 and with the compressed gas propellant before the valve assembly 205 and dip tube 116 are clinched onto the container curl 117 by use of conventional clinching equipment to make a gas-tight seal between the valve assembly 205 and the container 118. The container 118 is then pressurized to the desired working pressure by gassing through the stem orifice 105. When the stem 107 is depressed by more than approximately 1 mm through application of external force, the stem gasket 104 deforms away from the side hole in the stem gasket seat 106 area, opening a path between the container 118 and the external environment. When this external force is released, the spring 108 returns the stem to its fully closed position.

A valve assembly 205 can be clinched on to the top of the container 118 after filling with the hairspray composition. The stem orifice 105 is the outlet of the stem 107. The container 118 comprises a container wall 201 and a reservoir 204 for storing a hairspray composition and a compressed gas propellant. Activation of the valve assembly 205 is achieved by through application of external force to depress the engaged stem 107 and thereby releasing the hairspray composition and propellant into the external environment via a nozzle (not shown), which is sized to engage with the valve assembly 205. The valve assembly 205 comprises a housing 109 which mounts the dip tube 116 and which admits propellant gas from reservoir 204 into the flow of hairspray composition which rises up the dip tube 116 on operation of valve assembly 205 opening. FIG. 3A is valve assembly 200 that can be incorporated into the aerosol spray devices of FIGS. 1 and 2.

The valve assembly 200 comprises a housing 202 with internal walls defining a valve chamber 304, and a valve stem 220. The housing 202 is formed of two portions: a lower, cup portion 206; and an upper, cap portion 208. The valve assembly 200 would be crimped in place at the top of a container, with a distal portion of the valve stem 220 projecting from the top of the container for connection to an actuator.

The cup portion 206 has a lower wall 210 with an aperture 212 therethrough. A tubular spigot 214 depends from the lower wall 210. A dip tube (not shown) would be connected to the tubular spigot 214, typically by means of an enlarged lower end, the dip tube extending to the base of the container to which the valve assembly 200 is fitted. It will be appreciated that the lower region of a container to which the valve assembly 200 is fitted is in communication with the valve chamber 304 via the dip tube, spigot 214 and aperture 212 (which provides a liquid inlet for the valve chamber).

Figure 4A:
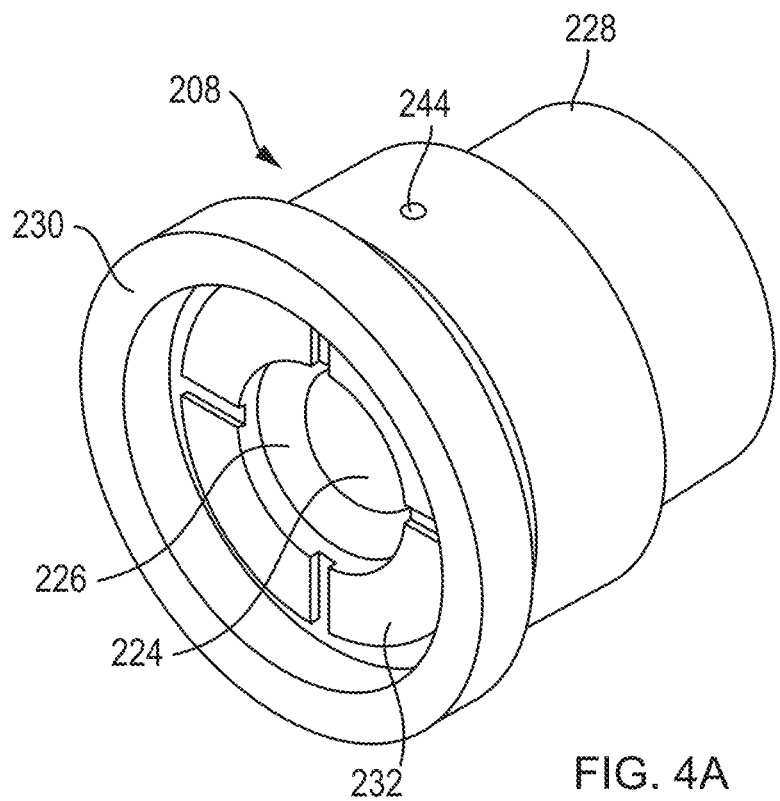
FIGS. 4A and 4B are perspective views of a cap part of the valve housing, showing gas flow conduits.

The cap portion 208, shown in FIG. 4A, comprises a generally cylindrical inner wall 224 from which a lip 226 projects inwardly at the upper end thereof. The lower end 228 of the cap portion has a narrower outer diameter so as to fit with an interference fit inside the cup portion 206. At the upper end of the cap portion 208, an annular rim 230, together with an upper surface 232, defines a shelf within which an annular sealing gasket 260 sits.

Figure 4B:
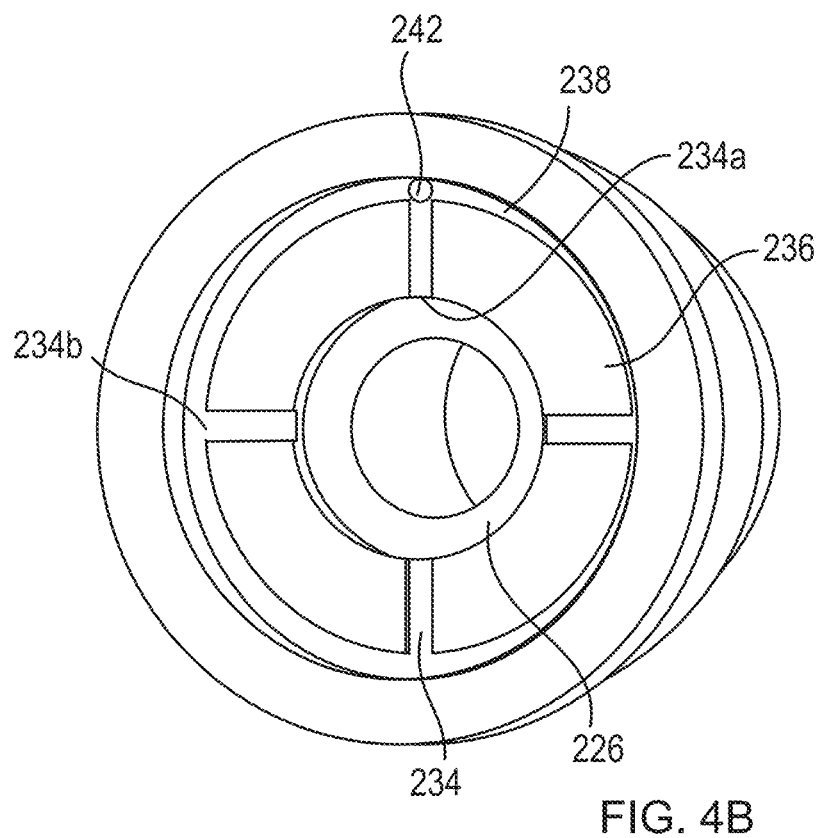

FIG. 4B shows a plurality of radial grooves 234 are defined between corresponding radial ribs 236 on the upper surface 232. Inner ends 234a of the grooves 234 open into the upper end of the valve chamber, above the lip 226. Outer ends 234b of the grooves 234 open into a circumferential groove 238, which circumscribes the upper surface 232 just inside the rim 230. The lower and side surfaces of the respective grooves 234, 238 are formed by the cup portion itself, whereas the upper surfaces thereof are formed by the lower surface 262 of the gasket 260.

A conduit 240 is formed through the cap portion 208, with an upper end opening into the circumferential groove 238 via a hole 242, and with a lower end exiting the side of the cup portion via a hole 244 in the outer surface thereof. It will be appreciated that the head space of a container to which the valve assembly 200 is fitted is in communication with the valve chamber 304 via the conduit 240, circumferential groove 238 and radial grooves 234 (which together provide a gas inlet for the valve chamber).

The valve stem 220 is generally cylindrical, having an outer surface 272 with a diameter equal to the inner diameter of the lip 226 such that the lip 226 forms a seal around the perimeter of the valve stem. A proximal end 274 of the valve stem is received in the valve chamber 304 and a distal end 276 projects through the centre 264 of the annular sealing gasket 260, which is dimensioned to seal against the outer surface 272 of the valve stem 220. The lower surface 262 of the gasket 260 defines the top of the valve chamber 304. The gasket 260, lip 226 and outer surface 272 of the valve stem 220 form a sealed opening 211 in the valve chamber 304.

The valve stem 220 includes an outlet flow conduit 280 with an orifice 282 at the distal end 276 and, more proximally, at least one first stem inlet 284 for liquid and at least one second stem inlet 286 for gas. As illustrated, there is a single stem inlet 284 for liquid and a single stem inlet 286 for gas, and they are positioned roughly in the middle of the valve stem, with the gas inlet 286 being slightly distal of the liquid inlet 284. It will be understood that alternative arrangements are envisaged. For example, there could be multiple liquid inlets 284 and/or multiple gas inlets 286; the inlets 284, 286 could be located more proximally or more distally than shown; and the axial separation between the respective liquid and gas inlets could be greater than shown.

Figure 5A:
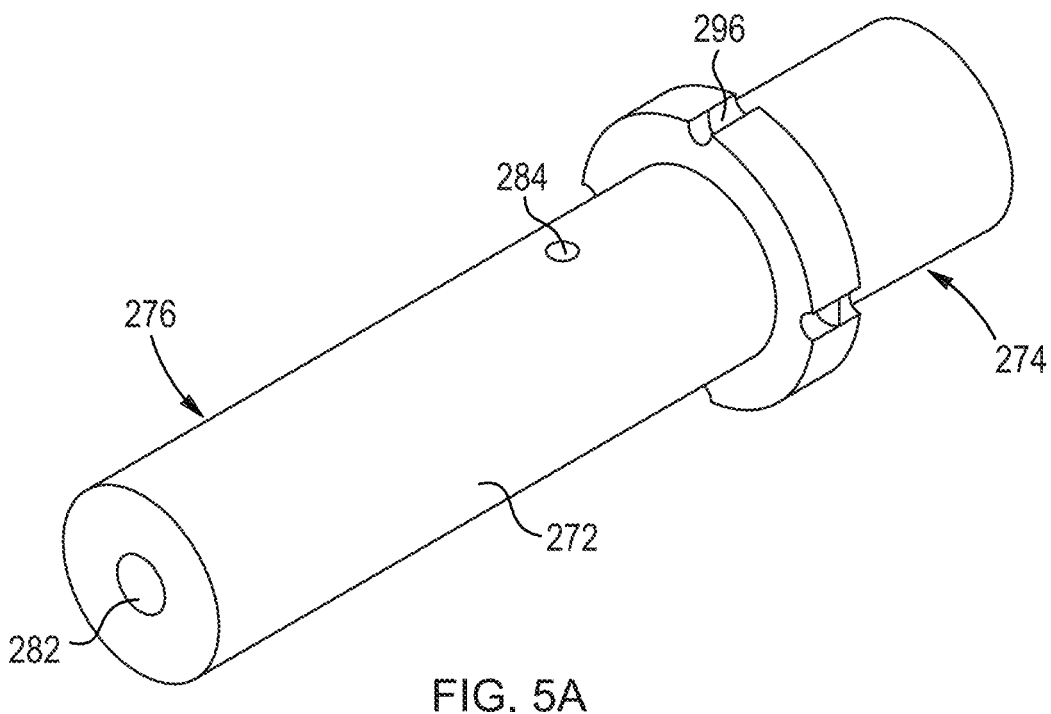
FIG. 5A is a perspective view of a stem forming part of the valve assembly in accordance with the invention.
Figure 5B:
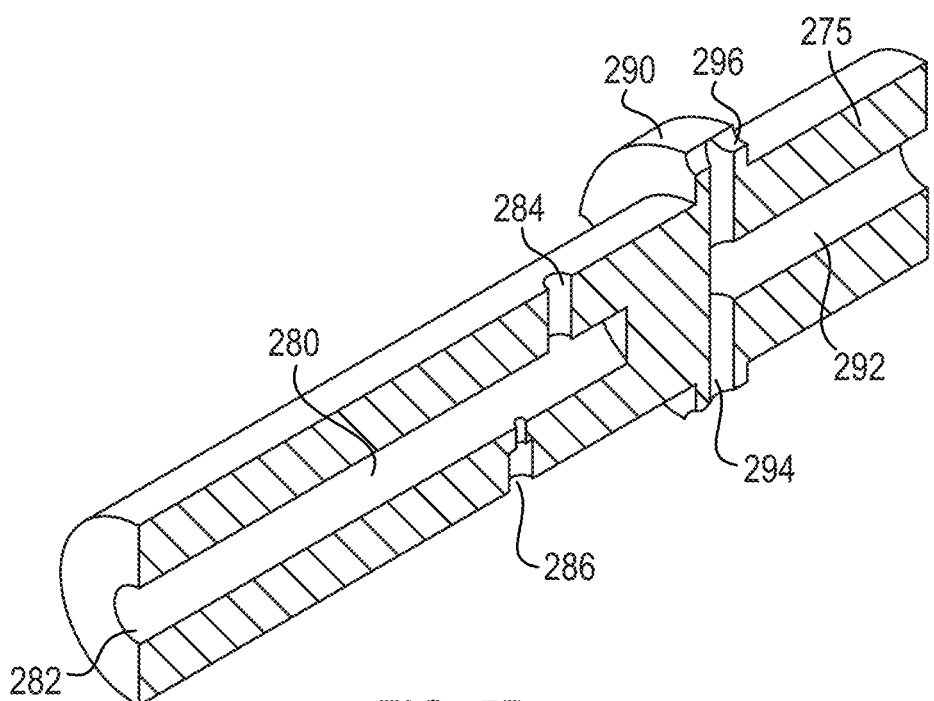
FIG. 5B is a cross section through the stem of FIG. 5A.

As shown in FIGS. 5A and 5B, towards the proximal end 274 of the valve stem 220, an enlarged shoulder portion 290 projects radially from the cylindrical valve stem 220. The diameter of the shoulder 290 is substantially equal to that of the valve chamber 304. A bore 292 runs centrally from the proximal end face 275 valve stem 220 to the shoulder portion 290. Four conduits 294 extend radially within the shoulder portion 290 from the centre, where they open into the bore 292, to the outside. At the outer ends, the radial conduits 294 open into respective axial grooves 296 in the outer surface of the shoulder 290 that run parallel to the bore 292 and to the outlet conduit 280.

As shown in the drawings, the valve stem 220 is biased upwardly of the valve assembly (and thus of the aerosol device) by means of a coil spring 222. Lower end of coil spring 222 locates around the aperture 212 of the cup portion 206 of the housing 202. In the closed valve position, as shown in FIG. 3A, the shoulder 290 abuts against the lip 226 under the force of the spring 222, and the flow channel defined by the bore 292, radial conduits 294 and axial grooves 296 is blocked by virtue of the tops of the axial grooves 296 abutting against the underside of the lip 226. Furthermore, the liquid inlet 284 is more distal than the sealing gasket 260. Accordingly, there is no fluid communication between the valve chamber liquid inlet 212 and the outlet conduit 280. There is also no fluid communication between the valve chamber gas inlet 234a and the outlet conduit 280, because the gas inlet 286 is also more distal than the sealing gasket 260, which hermetically seals against the outer surface 272 of the valve stem.

The abutment of the shoulder 290 against the lip 226 acts as an upper limit stop, preventing the valve stem 220 from being urged further out of the valve housing 202.

Figures 3B, 3C:
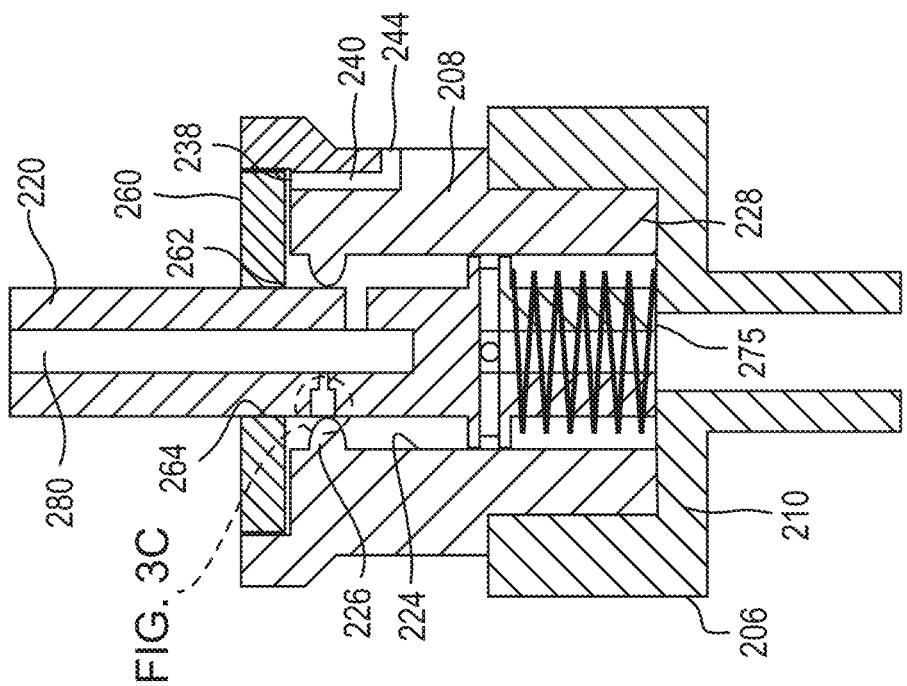
FIGS. 3A and 3B schematically illustrate a valve assembly in accordance with the invention in respective closed and open positions.
FIG. 3C is a detail view of part of FIG. 3B, showing the relative positions of an annular lip and a stem gas inlet.
Figure 3A:
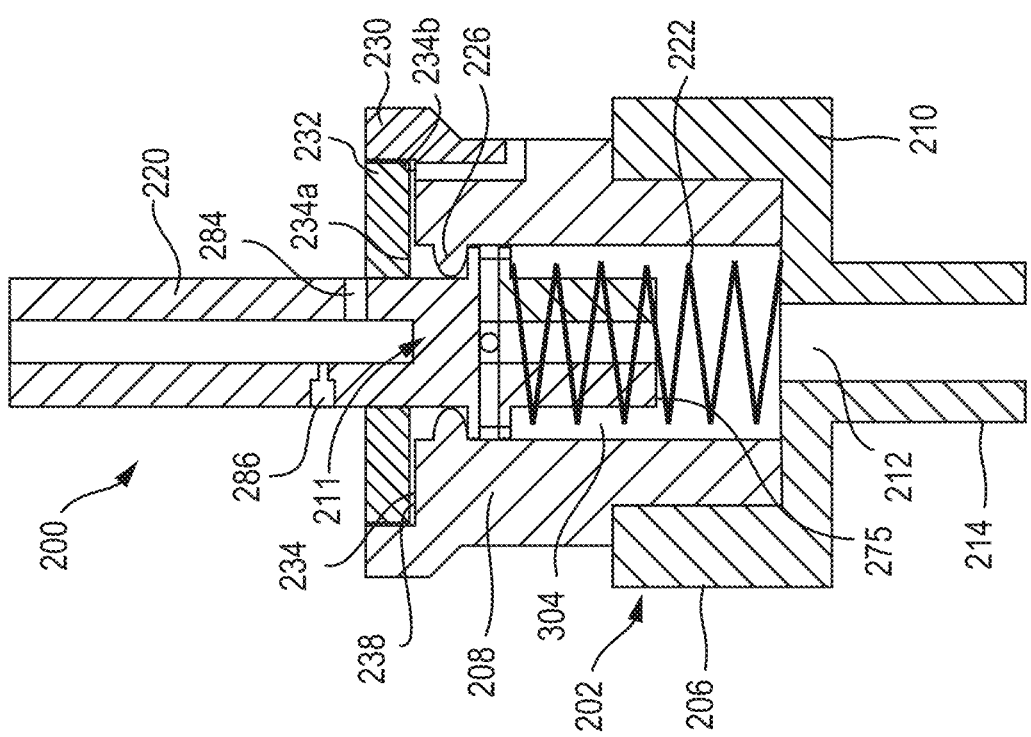
Figure 3C:
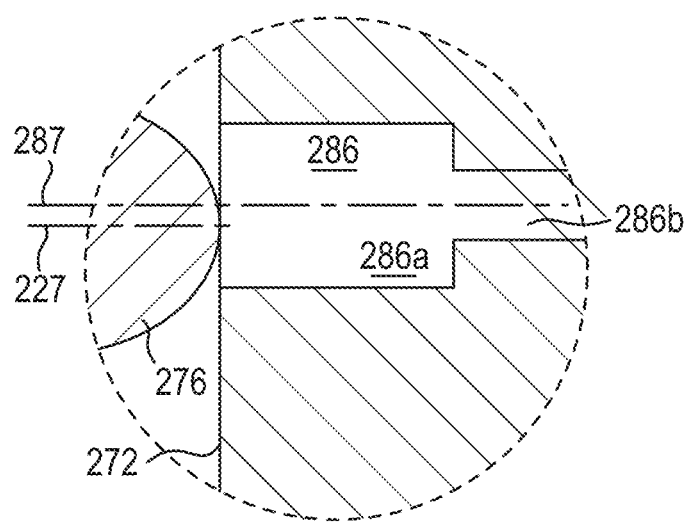

When the valve stem is moved to the open position, as shown in FIG. 3B, the stem liquid inlet 284 is moved below (i.e. proximal of) the lip 226 so as to be in fluid communication with the valve chamber liquid inlet 212 via the flow channel defined by the bore 292, radial conduits 294 and axial grooves 296 through the stem shoulder portion 290. Also, the stem gas inlet 286 is moved below (i.e. proximal of) the sealing gasket 260 to a position at the upper end of the valve chamber 304 in fluid communication with the valve chamber gas inlet 234a. At least a part of the stem gas inlet 286 must be open to the upper portion of the valve chamber 304 (i.e. the portion above the lip 226). Abutment of the bottom face 275 of the valve stem 220 against the lower wall 210 of the cup portion 206 defines a lower limit stop.

Thus, to operate the device, an actuator cap is depressed so that the valve stem 220 moves downwardly against the bias of spring 222 from the closed position to the open position. As a result, the liquid and gas stem inlets 284, 286 are displaced past the gasket 260 and brought into respective fluid communication with liquid hairspray composition from the container 2 and compressed gas from the head space. Compressed gas can now flow into the outlet conduit 280 by passage through the hole 244 in the outer surface of the cap portion 208, the conduit 240, the hole 242, the circumferential groove 238 and radial grooves 234, and through the stem gas inlet 286.

Hairspray composition can now flow into the upper portion of the valve chamber 304 by passage upwardly along the dip tube 20, through the inlet 212, the bore 292, the radial conduits 294 and the axial grooves 296. Hairspray composition introduced into the upper portion of the valve chamber 304 passes via stem liquid inlet 284 into flow conduit 280 where it is mixed with the compressed gas bled through the stem gas inlet 286. A bubble laden flow of homogeneous bubbles with similar diameters (Dv50) and without significant coalescence or stratification is formed in the outlet flow conduit 280. That bubbly flow can then flow, preferably undisturbed, through the stem orifice and actuator.

Hairspray Compositions

The product relates to an aerosol hairspray product comprising: a container comprising a reservoir for a hairspray composition and a gas propellant, and a spraying device attached to the container. In some examples, the compressed gas propellant and hairspray composition are not stored in separate compartments. The reservoir can include from about 50% about to about 65% hairspray composition, or from about 55% to about 60% hairspray composition, by volume. The reservoir can include from about 35% to about 70% propellant, alternatively from about 40% to about 60% propellant, alternatively from about 45% to about 55% propellant, and alternatively from about 45% to about 50% propellant, by volume. As used herein, albeit unless otherwise stated, details of the hairspray composition refers to the composition before it is placed into the can. The same is true where details of the propellant are mentioned, unless otherwise stated.

The product is an aerosol hairspray product and thus does not include mousse products or any pump spray products.

The aerosol hairspray product is for spraying an ejected composition wherein the ejected composition consists of particles having an average particle size distribution (Dv50) of from 40 micron to 100 micron, alternatively from about 40 micron to about 90 micron, alternatively from about 60 micron to about 90 micron, as determined by the Particle Size Distribution Test Method, described hereafter. The aerosol hairspray product can be an ethanol-based hairspray product for spraying at a delivery rate, wherein the delivery rate is from about 0.2 g/s to about 0.9 g/s, alternatively from about 0.25 g/s to about 0.8 g/s, alternatively from about 0.28 g/s to about 0.75 g/s, and alternatively from about 0.3 g/s to about 0.7 g/s, as determined by the Delivery Rate Test Method, described hereafter. The aerosol hairspray product can be an ethanol-free hairspray product for spraying at a delivery rate, wherein the delivery rate is from about 0.2 g/s to about 0.6 g/s, alternatively from about 0.25 g/s to about 0.55 g/s, and alternatively 0.3 g/s to about 0.5 g/s, as determined by the Delivery Rate Test Method, described hereafter.

The kinematic viscosity of the hairspray composition, in particular the ethanol-free hairspray composition, without propellant can be from about 0.5 cSt, or from about 1 cSt, or from about 1.25 cSt, or from about 1.5 cSt, or from about 1.75 cSt, or from about 1.8 cSt to about 5.5 cSt, to about 5 cSt, or to about 4.5 cSt, or to about 4 cSt, or to about 3.5 cSt, or to about 3 cSt, or to about 2.5 cSt, or to about 2.3 cSt, or to about 2.2 cSt, or to about 2.1 cSt, or to about 2.0 cSt.

The kinematic viscosity of the hairspray composition, in particular the ethanol-based hairspray, without propellant can be from about 1 cSt to about 20 cSt, alternatively from about 3 cSt to about 18 cSt, and alternatively from about 5 to about 15 cSt.

The hairspray composition can include from about 1.5% to about 10% hairstyling polymer, by weight of the hairspray composition. The amount of hairstyling polymer is important in balancing hold performance and on-hair wetness. The amount of hairstyling polymer drives the hold performance but is limited by a maximum sprayable viscosity. The hairspray composition can include from about 2%, or from about 8%, or from about 3%, or from about 7%, or from about 3.5% to about 6% hairstyling polymer, by weight of the hairspray composition. These amounts may be the total amount of hairstyling polymer in the hairspray composition.

The hairstyling polymer or mixture of hairstyling polymers can be water-soluble hairstyling polymers and/or ethanol/alcohol-soluble hairstyling polymers that can provide a viscosity of about 6 cSt or less as measured before the addition of propellant. This hairspray composition containing soluble hairstyling polymer(s) is then pressurized in a can with a gas propellant. In some examples, a user may shake the can prior to dispensing in order to mix the hairspray composition with the hairstyling polymer and the propellant.

The hairstyling polymer may be any water-soluble or alcohol-soluble film-forming polymer or mixture of such polymers. This includes homopolymers or copolymers of natural or synthetic origin having functionality rendering the polymers water-soluble such as hydroxyl, amine, amide or carboxyl groups.

The soluble hairstyling polymers when diluted at the range claimed, can form transparent or semi-transparent stable solutions. Depending on the specific polymer type, it may be necessary to adjust the pH of the formulation or to neutralize the formulation after addition of the polymer to water to achieve water solubility. The hairstyling polymer may be classified into two types, (totally) synthetic polymers and natural products together with their chemically modified derivatives and further can be grouped into three main headings; naturally occurring, semi-synthetic and completely synthetic polymers. The hairstyling polymer can be selected from the group consisting of: cationic hairstyling polymers, anionic hairstyling polymers, nonionic hairstyling polymers, and amphoteric hairstyling polymers. The molecular weight of the hairstyling polymers should be such that the hairspray composition without propellant meets the viscosity requirement range specified. The hairstyling polymers can be linear or branched.

The hairstyling polymer may be a cationic hairstyling polymer or a mixture of cationic hairstyling polymers. The cationic hairstyling polymer can be selected from the group consisting of: quaternized acrylates or methacrylates; quaternary homopolymers or copolymers of vinylimidazole; homopolymers or copolymers comprising a quaternary dimethdiallyl ammonium chloride; non-cellulosic cationic polysaccharides; cationic cellulose derivatives; chitosans and derivatives thereof; and mixtures thereof.

The cationic hairstyling polymer may be selected from quaternized acrylates or methacrylates. The cationic hairstyling polymer can be a copolymer comprising: a) at least one of: quaternized dialkylaminoalkyl acrylamides (e.g. Quaternized dimethyl amino propyl methacrylamide); or quaternized dialkylaminoalkyl acrylates (e.g. quaternized dimethyl aminoethyl methacrylate) and b) one or more monomers selected from the group consisting of: vinyllactams such as vinylpyrrolidone or vinylcaprolactam; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; and allyl esters or methallyl esters. The counter ion can be either a methosulfate anion or a halide such as chloride or bromide.

The cationic hairstyling polymer may be a quaternary homopolymer or copolymer of vinylimidazole. The cationic hairstyling polymer can be a copolymer comprising a) a quaternized vinylimizazole and b) one or more other monomers. The other monomer may be selected from the group consisting of: vinyllactams such as vinylpyrrolidone or vinylcaprolactam such as vinylpyrrolidone/quaternized vinylimidazole (PQ-16) such as that sold as Luviquat FC-550 by BASF; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

The cationic hairstyling polymer may include a dimethdiallyl ammonium chloride. In The cationic hairstyling polymer can be a homopolymer or copolymer comprising a quaternary dimethdiallyl ammonium chloride and another monomer. Such other monomer may be selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcaprolactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

The cationic hairstyling polymer can be a non-cellulosic cationic polysaccharide. The cationic hairstyling polymer can be a guar gums such as those containing trialkylammonium cationic groups. For example, such as guar hydroxypropyltrimonium chloride, which is available as N-Hance™ 3269 from Ashland™.

The cationic hairstyling polymer can be a cationic cellulose derivative. The cationic hairstyling polymer can be copolymers of cellulose derivatives such as hydroxyalkylcelluloses (e.g. hydroxymethyl-, hydroxyethyl- or hydroxypropylcelluloses) grafted with a water-soluble monomer comprising a quaternary ammonium (e.g. glycidytrimethyl ammonium, methacryloyloxyethyltrimethylammonium, or a methacrylamidopropyltrimethylammonium, or dimethyldiallylammonium salt). For example, such as hydroxyethylcellulose dimethyldiallyammonium chloride [PQ4] sold as Celquat® L200 by Akzo Nobel®, or such as Quaternized hydroxyethylcellulose [PQ10] sold as UCARE™ JR125 by Dow® Personal Care. The cationic hairstyling polymer can be selected from chitosans and derivatives thereof. A derivative of a chitosan includes salts of chitosans. The salts can be chitosan acetate, lactate, glutamate, gluconate or pyrrolidonecarboxylate preferably with a degree of hydrolysis of at least 80%. A suitable chitosan includes Hydagen® HCMF by BASF®.

The hairstyling polymer can be an anionic hairstyling polymer or a mixture of anionic hairstyling polymers. The anionic hairstyling polymer can be selected from those comprising groups derived from carboxylic or sulfonic acids. Copolymers containing acid units are generally used in their partially or totally neutralized form, more preferably totally neutralized. The anionic hairstyling polymer can comprises\: (a) at least one monomer derived from a carboxylic acid such as acrylic acid, or methacrylic acid or crotonic acid or their salts, or C4-C8 monounsaturated polycarboxylic acids or anhydrides (e.g. maleic, furamic, itaconic acids and their anhydrides) and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylaminoethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated. The anionic hairstyling polymer can comprise monomers derived from a sulfonic acid. Anionic polymers can comprise: (a) at least one monomer derived from a sulfonic acid such as vinylsulfonic, styrenesulfonic, naphthalenesulfonic, acrylalkyl sulfonic, acrylamidoalkylsulfonic acid or their salts and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated.

The anionic hairstyling polymer can be a water-soluble polyurethane.

The anionic hairstyling polymers can be selected from: copolymers derived from acrylic acid such as the acrylic acid/ethylacrylate/N-tert-butylacrylamide terpolymer such as that sold as Ultrahold 8 by BASF®; Octylacrylamide/Acrylates/Butylaminoethyl/Methacrylate Copolymer such as that sold as Amphomer® by Akzo Nobel®; methacrylic acid/ester acrylate/ester methacrylate such as that sold as Balance® CR by Akzo Nobel®; Octylacrylamide/Acrylates/Butylaminoethyl Methacrylate Copolymer such that sold as Balance® 47 by Akzo Nobel®; methacrylic acid/hydroxyethylmethacrylate/various acrylate esters such as that known as Acudyne™ 1000 sold by Dow® Chemical; acrylates/hydroxyethylmethacrylate such as that sold as Acudyne™ 180 by Dow® Chemical; methacrylic acid/hydroxyethylmethacrylate/various acrylate esters such as that sold as Acudyne™ DHR by Dow® Chemical; n-butyl methacrylate/methacrylic acid/ethyl acrylate copolymer such as that sold as Tilamar® Fix A-1000 by DSM®; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resyn™ 28-2930 by Akzo Nobel®. Hairstyling polymers derived from sulfonic acid can include: sodium polystyrene sulfonate sold as Flexan® 130 by Ashland™; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman. The anionic hairstyling polymers can be selected from: copolymers derived from acrylic acid such as the acrylic acid/ethylacrylate/N-tert-butylacrylamide terpolymers (such as that sold as Ultrahold® 8 by BASF®); Octylacrylamide/Acrylates/Butylaminoethyl/Methacrylate Copolymer such as that sold as Amphomer; methacrylic acid/ester acrylate/ester methacrylate such as that sold as Balance® CR by Akzo Nobel®; Octylacrylamide/Acrylates/Butylaminoethyl Methacrylate Copolymer such as that sold as Balance® 47 by Akzo Nobel®; methacrylic acid/hydroxyethylmethacrylate/various acrylate esters such as that known as Acudyne® 1000 sold by Dow® Chemical; acrylates/hydroxyethylmethacrylate such as that sold as Acudyne® 180 by Dow® Chemical; methacrylic acid/hydroxyethylmethacrylate/various acrylate esters such as that sold as Acudyne® DHR by Dow® Chemical; n-butyl methacrylate/methacrylic acid/ethyl acrylate copolymer such as that sold as Tilamar® Fix A-1000 by DSM®; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resyn™ 282930 by Akzo Nobel®. Hairstyling polymers derived from styrene sulfonic acid can include: sodium polystyrene sulfonate sold as Flexan® 130 by Ashland™; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman.

The hairstyling polymer can be an anionic hairstyling polymer, and wherein the anionic hairstyling polymer is selected from: copolymers derived from acrylic acid such as the acrylic acid/ethylacrylate/N-tert-butylacrylamide terpolymers; Octylacrylamide/Acrylates/Butylaminoethyl/

Methacrylate Copolymers; methacrylic acid/ester acrylate/ester methacrylates; Octylacrylamide/Acrylates/Butylaminoethyl Methacrylate Copolymer; methacrylic acid/hydroxyethylmethacrylate/various acrylate esters; acrylates/hydroxyethylmethacrylate; methacrylic acid/hydroxyethylmethacrylate/various acrylate esters; n-butyl methacrylate/methacrylic acid/ethyl acrylate copolymers; copolymers derived from crotonic acid, such as vinyl acetate/vinyl tertbutylbenzoate/crotonic acid terpolymers; and the crotonic acid/vinyl acetate/vinyl neododecanoate terpolymers; and mixtures thereof.

The hairstyling polymer can be a polyurethane dispersed in solvent (e.g. water, ethanol, or another alcohol). Such polyurethanes can include those such as adipic acid, 1-6 hexandiol, neopentyl glycol, isophorone diisocyanate, isophorone diamine, N-(2-aminoethyl)-3-aminoethanesulphonic acid, sodium salt (also known as Polyurethane-48) such as that sold as Baycusan® C1008 by Bayer®; and such as isophorone diisocyanate, dimethylol propionic acid, 4,4-isopropylidenediphenol/propylene oxide/ethylene oxide (also known as Polyurethene-14) such as that sold as a mixture under the name of DynamX® H₂O by Akzo Nobel®.

The hairstyling polymer can be a nonionic hairstyling polymer or a mixture of nonionic hairstyling polymers. Suitable synthetic non-ionic hairstyling polymers can include: homopolymers and copolymers comprising: (a) at least one of the following main monomers: vinylpyrrolidone; vinyl esters grafted onto a polyalkylene glycol such as polyethylene glycol; acrylate esters grafted onto a polyalkylene glycol such as polyethylene glycol or acrylamide and (b) one or more other monomers such as vinyl esters (e.g. vinyl acetate or vinyl propionate, vinyl tert-butyl-benzoate); alkylacrylamine (e.g. tert-butylamino-ethyl methacrylate, dimethyl aminoethyl methacrylate); vinylcaprolactam; hydroxyalkylated acrylamide; amino alkylated acrylamide (e.g. dimethyl amino propyl methacrylamide); vinyl ether; alkyl maleimide, hydroxyalkyl maleimide (e.g. Ethyl/Ethanol Maleimide).

The non-ionic hairstyling polymer can be selected from vinylpyrrolidone/vinyl acetate copolymers (such as that sold as Luviskol® VA 64 by BASF® and such as vinylpyrrolidone homopolymer such as that sold as PVP K30 by Ashland™).

The non-ionic hairstyling polymer can be a water-soluble natural polymer being a cellulose derivative, such as hydroxyalkylcelluloses (e.g. hydroxymethyl-, hydroxyethyl- or hydroxypropylcelluloses) and starches.

The hairstyling polymer can be an amphoteric hairstyling polymer or a mixture of amphoteric hairstyling polymers. Suitable synthetic amphoteric hairstyling polymers include those comprising: an acid and a base like monomer; a carboxybetaine or sulfobetaine zwitterionic monomer; and an alkylamine oxide acrylate monomer. The amphoteric polymers can comprise (a) at least one monomer containing a basic nitrogen atom such as a quaternized dialkylaminoalkyl acrylamide (e.g. Quaternized dimethyl amino propyl methacrylamide) or a quaternized dialkylaminoalkyl acrylate (e.g. quaternized dimethyl aminoethyl methacrylate) and (b) at least one acid monomer comprising one or more carboxylic or sulfonic groups such as acrylic acid, or methacrylic acid or crotonic acid or their salts, or C4-C8 mono-unsaturated polycarboxylic acids or anhydrides (e.g. maleic, furamic, itaconic acids and their anhydrides) and (c) one or more monomers selected from acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The amphoteric hairstyling polymer can comprise at least one carboxybetaine or sulfobetaine zwitterionic monomer such as carboxybetaine methacrylate and sulfobetaine methacrylate. The amphoteric hairstyling polymer can comprise: (a) at least one carboxybetaine or sulfobetaine zwitterionic monomer such as carboxybetaine methacrylate and sulfobetaine methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The amphoteric hairstyling polymer can comprise at least an alkylamine oxide acrylate. The amphoteric hairstyling polymer can comprise: (a) an ethylamine oxide methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly (ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. An example of such an amphoteric hairstyling polymer is acrylates/ethylamine oxide methacrylate sold as Diaformer® Z 731 N by Clariant®.

The hairstyling polymer can be selected from the group consisting of: acrylates copolymers of two or more monomers of (meth)acrylic acid or one of their simple esters; octylacrylamide/acrylate/butylaminoethyl methacrylate copolymers; acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof.

The hairspray composition can be substantially free of water-insoluble polymers and/or alcohol-insoluble polymers. Polymers that are not miscible in water may be avoided. Polymers of high molecular weight (>200,000 g/mol) may be avoided or only used at very low levels such that the hairspray composition does not exceed the viscosity requirements. The hairspray composition may be substantially free of a polymer having a molecular weight of greater than 200,000 g/mol. The hairspray composition may be substantially free of a polymer comprising at least two long hydrophobic (e.g. linear fatty chains of 10 carbons or more) grafts. Such polymers with such grafts can lead to associative interactions in the hairspray composition which can drive viscosity up without contributing to the strength of the film delivered to the hair.

The hairspray composition can include a panthenol compound and/or a silicone compound. The panthenol compound may be selected from the group consisting of: panthenol, a pantothenic acid derivative, and mixtures thereof. The panthenol compound can be selected from the group consisting of: D-panthenol ([R]-2,4-dihydroxy-N-[3-15-(hydroxypropyl)]-3,3-dimethylbutamide), D/L-panthenol, pantothenic acids and their salts, panthenyl triacetate, royal jelly, panthetine, pantotheine, panthenyl ethyl ether, pangamic acid, pantoyl lactose, Vitamin B complex, and mixtures thereof. The panthenol compound can be useful in view of providing excellent hair look and feel benefits. The hairspray composition may comprise from about 0.1% to about 0.6%, or from about 0.1% to about 0.3%, of a panthenol compound, by weight of the hairspray composition.

The hairspray composition can include a silicone compound. The silicone can be useful because it gives a smoother feel and also shine to the hair. The silicone compound can be a dimethicone compound. In The silicone compound can be a PEG dimethicone, for example PEG-12 dimethicone.

The hairspray composition may further include a surfactant. The hairspray composition may include 1% or less surfactant, or 0.6% or less, or 0.4% or less, or 0.3% or less, by weight of the hairspray composition. The surfactant may be selected from the group consisting of cationic surfactants, non-ionic surfactants, anionic surfactants, and mixtures thereof. Cationic surfactants may be selected from the group consisting of cetrimonium chloride (e.g. Quartamin® 60L-G from Kao®; DEHYQUART A-CA/DETEX; ARQUAD 16-25 LO); cocamidopropyl hydroxysultaine (e.g. REWOTERIC® AM CAS); cocamidopropyl betaine (e.g. TEGO® BETAIN F 50); betaine; and mixtures thereof. Non-ionic surfactants may be selected from the group consisting of: castor oil PEG-40 H (e.g. NEODOL® 10 91-8); laureth-4 (e.g. DEHYDOL® LS 4 DEO N); laureth-9; decyl glucoside (e.g. Plantacare® 2000); polysorbate 20 (e.g. TWEEN 20 PHARMA from UNIQEMA); PEG-25 hydrogenated castor oil (e.g. SIMULSOL™ 1292 DF from SEPPIC®); PEG-40 hydrogenated castor oil (e.g. CREMOPHOR® CO 410 from BASF®); PPG-1-PEG-9-laurylglycolether (e.g. Eumulgin® L); siloxane polyalkyleneoxide copolymer (Silwet® L7604 from Momentive®); and polydimethylsiloxane methylethoxylate (Silwet® L7600 from Momentive®); and mixtures thereof. A suitable anionic surfactant is dioctyl sodium sulfosuccinate (DOSS or 1,4-dioctoxy-1,4-dioxobutane-2-sulfonic acid), an example of which is Aerosol® OT-70 PG from Cytec. The surfactant can be selected from the group consisting of: castor oil PEG-40 H; cetrimonium chloride; laureth-4; laureth-9; decyl glucoside; cocamidopropyl hydroxysultaine; polysorbate 20; siloxane polyalkyleneoxide copolymer; dioctyl sodium sulfosuccinate; and mixtures thereof.

The hairspray composition can include a neutraliser. Suitable neutralisers may include potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia (NH3), triethanolamine, trimethylamine (Tris AminoUltra), aminomethylpropandiol (AMPD). The neutralising agent can be 2-aminobutanol, ammonia, or 2-aminomethyl propanol.

The hairspray composition may include at least one preservative. The preservative may be present in an amount of less than about 1.5%, or 0% to 1%, or 0.01% to 1%, by weight of the hairspray composition. Suitable preservatives may include: phenoxyethanol (e.g. Euxyl® PE 9010), benzyl alcohol, propylene glycol, PHMB (Poly-aminopropyl biguanide), Optiphen (Phenoxyethanol+caprylyl glycol) from ISP, Symtriol (1,2-octanediol and 1,2 hexanediol, methylbenzyl alcohol) from Symrise, octylsalicylate, 1,3-bis(hydroxymethyl)-5,5-dimethylimidazolidine-2,4-dione (DMDM hydantoin; Nipaguard® DMDMH by Clariant), EDTA (Rexat), butylene glycol (Dekaben LMB), and parben types e.g. methylparaben (e.g.PHB methyl ester from Schütz & Co., or SLI Chemicals, or Nipagin® M), propylparaben (PHB-propylester from Solvadis Specialties).

The hairspray composition may further include at least one perfume or fragrance. The hairspray composition may comprise a maximum of about 0.5% perfume or fragrance, or from about 0% to about 0.4%, or from about 0.03% to about 0.3%, by weight of the hairspray composition.

The hairspray composition may include a corrosion inhibitor. In one example, the corrosion inhibitor can be EDTA.

The hairspray composition can include vitamins and amino acids such as: water-soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their salts and/or derivatives, water insoluble amino acids such as tyrosine, tryptamine, viscosity modifiers, dyes, non-volatile solvents or diluents (water soluble and insoluble), pearlescent aids, foam boosters, additional surfactants or non-ionic cosurfactants, pediculocides, pH adjusting agents, perfumes, preservatives, chelants, proteins, skin active agents, sunscreens, UV absorbers, vitamins, niacinamide, caffeine and minoxidil. The hairspray composition may include from about 0.01% to about 5% vitamins and/or amino acids, by weight of the hairspray composition. The hairspray composition may further comprise pigment materials such as inorganic pigments, nitroso-, monoazo-, disazo-compounds, carotenoid, triphenyl methane, triaryl methane, chemicals of the quinoline, oxazine, azine, or anthraquinone type, as well as compounds which are indigoid, thionindigoid, quinacridone, phthalocianine, botanical, natural colors, and water-soluble components. The hairspray composition may include from about 0.0001% to about 5% pigment materials, by weight of the hairspray composition. The hairspray composition may also contain antimicrobial agents which are useful as cosmetic biocides. The hairspray composition may comprise from about 0.01% to about 5% antimicrobial agents, by weight of the hairspray composition.

Ethanol-Based Hairspray

An ethanol-based hairspray composition can comprise an alcohol solvent. Concentrations of the alcohol solvent can range from about 50% to about 99.9%, alternatively from about 60% to about 97%, alternatively from about 70% to about 95%, alternatively from about 80% to about 95% alcohol, by weight of the hairspray compositions.

Alcohol solvents suitable for use in the hairspray compositions of the present invention are preferably ethanol, n-propanol, isopropanol, and combinations.

The hairspray composition may further comprise other additional solvents, including water, provided that such additional solvents are chemically and physically compatible with the ingredients of the composition and that it does not substantially and unduly impair product performance. The hairspray compositions may further comprise up to about 45% by weight of water, alternatively less than about 40%. Formulation examples and additional ingredients that can be used in an ethanol-based hairspray can be found in WO1998/05379, incorporated by reference.

Ethanol-Free Hairspray

Some consumers may prefer an ethanol-free or very low alcohol hairsprays because they can have a purer fragrance (in view of the absence of an alcohol smell), less observed hair dryness and reduced brittleness effects to the hair, and consumers may perceive them to be more environmentally friendly, and healthier to use.

The hairspray composition can contain less than about 2% ethanol, alternatively less than about 1% ethanol, alternatively less than about 0.5% ethanol, alternatively less than about 0.25% ethanol, by weight of the hairspray composition, or is substantially free of or free of ethanol. The hairspray composition can contain less than about 2% alcohol, alternatively less than about 1% alcohol, alternatively less than about 0.5% alcohol, alternatively less than about 0.25% alcohol, by weight of the hairspray composition, or is substantially free of or free of alcohol. The hairspray composition can be substantially free of or free of ethanol, isopropanol and propanol. The hairspray composition can contain about 1.8% or less, or about 1.5% or less, or about 1% or less, alcohol by weight of the hairspray composition. The hairspray composition can contain 1.8% or less, or about 1.5% or less, or about 1% or less, aliphatic alcohol by weight of the hairspray composition. "Aliphatic alcohol" as used herein means an alcohol comprising no aromatic group. The amount of alcohol is important because anything above very low levels of alcohol may leave the hair feeling dry and brittle and some alcohols may cause an allergic response in some users.

The hairspray composition can include from about 50% to about 99% water, by weight of the hairspray composition. The water can provide a solvent for the hairstyling polymer and other ingredients in the hairspray composition. Many useful ingredients for the hairspray composition dissolve in water i.e. are water soluble. In The hairspray composition can contain from about 50% to about 99% water, alternatively from about 60% to about 98% water, alternatively from about 70% to about 97% water, alternatively from about 80% to about 96% water, alternatively from about 85% to about 96% water, by weight of the hairspray composition. The compressed gas propellant can include gases such as nitrogen, air, carbon dioxide, nitrous oxide, and other inert gases.

Additional information on hairspray compositions and aerosol spray dispensers is found in U.S. Pat. Nos. 9,986,809, 10,131,488, and 10,426,979, incorporated by reference.

Test Methods

Delivery Rate

The delivery rate of may be determined following ASTM D 3069-94, "Standard Test Method for Delivery Rate of Aerosol Products." In this test, the delivery rate of the product is determined by measuring the mass lost in a given time period. This correlates with the quantity of material expelled though the valve and actuator combination in a given time period. In this case, the can is tested at room temperature (at 21° C.) and a duration of 2 sec to 10 sec for the actuation time. The delivery rate is then determined by the equation:

Delivery Rate (g/sec)=Mass loss (g)/Actuation time (sec)

If the delivery rate is greater than about 0.45 g/sec, then the on-hair drying time may be too long for consumer satisfaction. This is unique for the ethanol-free hairsprays described herein as compared to traditional ethanol-based hairsprays, typically traditional hairsprays containing volatile alcohol have delivery rates between about 0.55 g/sec to 0.85 g/sec. Delivery rate can typically be adjusted by altering the pressure inside the container (increased pressure correlates with faster delivery rate) and/or the orifices in the spraying device, such as the orifices in the nozzle, orifices in the valve, and the inner diameter of the diptube.

Particle Size Distribution

The droplet size through the life of the can may be important as it impacts the dry feel, dry time and hold performance of the hairspray. Smaller droplets dry faster. More small droplets feel less wet than fewer large droplets. For hold, a larger number of smaller droplets give more surface area coverage to provide an even coating of hair welds. If the droplets are too small they will not bridge hair together in weld points and won't hold. This may be important for alcohol-free hairsprays that do not have the fast evaporation drying advantage of ethanol formulas. Ethanol hairsprays have a much broader working droplet size range i.e. 30-130 um Dv50. An ethanol-free hairspray below 40 um Dv50 may have holding problems. An ethanol-free hairspray above ~80 um Dv50 may have a noticeably slow drying time and initial wet hair feel. The Dv90 represents, though much fewer, the largest droplets in the spray. Dv90's over 180 um that get larger, up to 400 um, over the life of the can may result in sprays that appear visually uneven, with larger and sputtering droplets. These large drops make the spray less misty and even. This may result in clumping of hair where those large drops land. These hair clumps may make the end finished hair results have an unnatural hair feel that is difficult to run fingers or a brush through.

The average particle size distribution (Dv50) may be important in view of ejected composition drying time, which must be consumer acceptable. Indeed, a smaller average particle size distribution (Dv50) may be useful in that more particles have a higher surface area to volume ratio, which means a faster drying time. On the other hand, a too low average particle size distribution (Dv50) may mean that not enough hairstyling polymer is provided to the hair to provide spot welds.

A Malvern Spraytec instrument is used to measure the particle size distribution. The Dv50 is the term to describe the maximum particle size diameter below which 50% of the sample volume possesses, also known as the median particle size by volume. The Dv90 is the term to describe the maximum particle size diameter below which 90% of the sample volume possesses. The Malvern Spraytec instrument uses the technique of laser diffraction for measurement of the size of the spray particles. The intensity of light scattered as a laser beam passes through a spray is measured. This data is then analysed to calculate the size of the particles that created the scattering pattern. A Malvern Spraytec 2000 is used according to the manufacturer's instructions. Test samples have a temperature between 20° C. to 22° C.

Viscosity Test Method

Kinematic viscosity may be measured by Ubbelohde tube. Kinematic viscosity is a measure of the resistance to flow of a fluid, equal to its absolute viscosity divided by its density. The SI unit of kinematic viscosity is $m^2 \cdot s^{-1}$. The cgs (centimeters/grams/seconds) physical unit for kinematic viscosity is the stokes (St), which can be expressed in terms of centistokes (cSt). 1 cSt=1 $mm^2 \cdot s^{-1} = 10^{-6}$ $m^2 \cdot s^{-1}$. Water at 20° C. has a kinematic viscosity of about 1 cSt. A Ubbelohde tube is a viscometer for measurement of kinematic viscosity of transparent Newtonian liquids by suspended level principle as described in ASTM D 445 and D 446, and ISO 3104 and 3105. For the Ubbelohde tube measure, there is no temperature effect on results, for other kinematic viscometers, temperatures different from specified test range can affect result. Herein, measurements were taken at a temperature of 20° C.+/−0.1° C. This method can be used to measure from about 0.6 cSt to 100 cSt. For instructions for the use of the Ubbelohde viscometer see ASTM D 445. Use Ubbelohde tube size 0 C for viscosities from 0.6 to 3 cSt at 20° C.+/−0.1° C. Use Ubbelohde tube size 1 for viscosities from 2 to 10 cSt at 20° C.+/−0.1° C. ASTM D445 is the "Standard Test Method for Kinematic Viscosity of Transparent and Opaque Liquids". ASTM D446 is "Specifications and Operating Instructions for Glass Capillary Kinematic Viscometers".

EXAMPLES

Aerosol dispensers were filled with either an ethanol-free hairspray (i.e. water-based hairspray) or an ethanol-based hairspray and 60% nitrogen propellant. Each experimental aerosol dispenser had an aerosol assembly that included one of four Salvalco Eco-Valves® that were identified by the insert color (pink, green, red, or blue). It is hypothesized that each Salvalco Eco-Valve® had different configurations that can include varying the exit orifice thickness and diameter and/or varying the number, height, and width of the channels tangential to the orifice. It is hypothesized that the different configurations can influence the spray properties.

The spray properties (e.g. spray rate (g/s) and droplet size (μm)) of the aerosol dispensers with the Salvalco Eco-Valves® were compared to a control (Pantene® Pro-V Airspray Flexible Hold Hairspray) throughout the life of the dispenser. Each insert/product combination was tested twice. The can was filled to 40-60% nitrogen at 135 PSIG. The cans were tested from 100% product (full can) to when 25% of the product was left in the can (end of can).

TABLE 2

| | Insert Color | Meets overall target spray properties in Table 1? | Does the aerosol product meet the target spray rate requires in Table 1? | Dv50 at full can (μm) | Is the Dv50 at end of can within 20 μm of the Dv50 at full can? |
|---|---|---|---|---|---|
| Ethanol-based hairspray (Table 7, Ex. J) | Green | Yes | Yes | 70 | Yes |
| | Pink | Yes | Yes | 70 | Yes |
| | Red | No | No | 79 | Yes |
| | Blue | No | No | 80 | Yes |
| Ethanol-free Hairspray (Table 5, Ex. A) | Green | Yes | Yes | 64 | Yes |
| | Pink | Yes | Yes | 63 | Yes |
| | Red | No | No | 72 | No |
| | Blue | No | No | 66 | No |

In the examples in Table 3 and Table 4, below, an aerosol container was filled with nitrogen gas and a hairspray composition. The aerosol container included the Salavaco Eco-Valve with the green insert. The hairsprays in Table 3 contain twice the concentration of actives and a higher viscosity, as compared to the paired example in Table 4.

The examples in Table 3 and Table 4, were tested to see if they met the properties described in Table 1, herein. The spray properties were maintained if the initial spray rate and Dv50 compared to the spray rate and Dv50 when 25% of the hairspray composition remained in the container varied by less than 10% and no more than 20 microns, respectively.

TABLE 3

Spray Rate and Dv50 of Ethanol-based and Ethanol-Free Hairsprays with a High Concentration of Actives

| | | 40% N$_2$ Fill | | 60% N$_2$ Fill | |
|---|---|---|---|---|---|
| | | Spray Rate (g/s) | Dv50 (μm) | Spray Rate (g/s) | Dv50 (μm) |
| Ethanol-based Hairspray (Table 7, Ex. JJ) | initial | 0.44 | 118 | 0.49 | 103 |
| | 25% of composition remaining | 0.38 | 141 | 0.48 | 108 |
| Ethanol-free Hairspray (Table 5, Ex. AA) | initial | 0.49 | 115 | 0.50 | 85 |
| | 25% of composition remaining | 0.43 | 115 | 0.47 | 93 |

None of the examples tested in

Table 3 meet all of the success criteria outlined herein. For the ethanol-based hairspray (Example JJ in Table 7, below) combined with 40% and 60% nitrogen propellant, the spray rate was consumer acceptable, however the Dv50 average particle size was too large to be a consumer acceptable hairspray product.

For the ethanol-free hairspray (Example AA in

Table 5, below), the spray rate was consumer acceptable for the examples with 40% and 60% nitrogen propellant. However, the particle size for these examples was outside the success criteria. For the 40% nitrogen propellant, the particle size was too large and for the 60% nitrogen propellant at both test points. For the 20% nitrogen propellant, the initial particle size was consumer acceptable, however when 25% of the composition was remaining, the average particle size was too large to be consumer acceptable.

Examples AA and JJ, which were tested in

Table 3, had a concentration of actives similar to current products that use a hydrocarbon propellant. It was found that since the nitrogen propellant did not liquefy, like a hydrocarbon propellant, a less concentrated hairspray composition could be used, while still providing excellent styling benefits. Additionally, since the Dv50 particle size for 40% nitrogen fill was too high for both ethanol-based and ethanol-free hairsprays and the Dv50 particle size for 60% was closer to the preferred range for both the initial and 25% of the product remaining, it was determined that 60% nitrogen would be used for the lower concentration formulas.

TABLE 4

Spray Rate and Dv50 of Ethanol-based and Ethanol-Free Hairsprays with a Lower Concentration of Actives

| | | 60% $N_2$ Fill | |
|---|---|---|---|
| | | Spray Rate, g/s | Dv50, μm |
| Ethanol-based Hairspray (Table 7, Ex. J) | initial | 0.42 | 70 |
| | 25% of composition remaining | 0.39 | 75 |
| Ethanol-free Hairspray (Table 5, Ex. A) | initial | 0.44 | 64 |
| | 25% of product remaining | 0.42 | 63 |

Examples J (

Table 7, below) and A (

Table 5, below) that were tested in Table 4 have half of the active level as compared to Examples JJ and AA, which were tested in Table 3. Both the ethanol-based hairspray (Example J) and the ethanol-free hairspray (Example A) have spray rates and Dv50 average particle size that are consumer acceptable at the initial spray and when 25% of the hairspray composition is remaining in the can.

The examples in

Table 5,

Table 6, and

Table 7 can be made using a conventional method of making hairspray compositions and products.

TABLE 5

Examples A-D Ethanol-Free Hairspray Compositions (active level %)

| | A | AA | B | C | D |
|---|---|---|---|---|---|
| Acrylates Copolymer [1] | 4.20% | 7.31% | 4.50% | 2.90% | 4.50% |
| Polyurethane-14/AMP-acrylates polymer blend [2] | 1.10% | 1.83% | 1.30% | 2.90% | — |
| Octylacrylamide/Acrylates/Butylaminoethyl/Methacrylate Copolymer [4] | 0.60% | 1.1% | — | — | — |
| Vinylpyrrolidone/Vinylacetate Copolymer [5] | — | — | — | — | — |
| Methacrylic acid/hydroxyethyl-methacrylate/various acrylate esters [3] | — | — | 0.60% | 1.50% | — |
| Polyquaternium-16 [6] | — | — | — | — | — |
| Chitosan [7] | — | — | — | — | — |
| Hydroxyethylcellulose dimethyldiallyammonium chloride[PQ4] [8] | — | — | — | — | — |
| 2-aminomethyl propanol (AMP) | 0.70% | 1.20% | 0.36% | 0.34% | 0.48% |
| Potassium Hydroxide | — | — | 0.48% | 0.45% | — |
| Fragrance | 0.08% | 0.16% | 0.10% | 0.10% | 0.10% |
| Dehyquart A-CA/Detex (cationic surfactant) | 0.1% | 0.2% | 0.2% | 0.2% | — |
| Dehydol LS 4 Deo N (Non-ionic surfactant) | 0.05% | 0.1% | 0.05% | 0.05% | — |
| PEG-12 dimethicone | 0.13% | 0.26% | — | 0.13% | — |
| Disodium EDTA | 0.11% | 0.22% | 0.11% | 0.11% | 0.11% |
| Phenoxyethanol | 0.50% | 1.00% | 0.50% | 0.50% | 0.50% |
| Methylparaben | 0.10% | 0.20% | 0.10% | 0.10% | 0.10% |
| Water | QS | QS | QS | QS | QS |

KEY:
[1] = Balance ® CR Polymer;
[2] = DynamX H20;
[3] = Acudyne 1000;
[4] = Amphomer;
[5] = Luviskol VA64;
[6] = Luviquat FC550;
[7] = Hydagen ® HCMF;
[8] = Celquat L-200.

TABLE 6

Examples E-I Ethanol-Free Hairspray Compositions (active level %)

| | E | F | G | H | I |
|---|---|---|---|---|---|
| Acrylates Copolymer [1] | 1.60% | — | — | — | — |
| Polyurethane-14/AMP-acrylates polymer blend [2] | 2.00% | — | — | — | — |
| Octylacrylamide/Acrylates/Butylaminoethyl/Methacrylate Copolymer [4] | — | 1.7% | — | — | — |
| Vinylpyrrolidone/Vinylacetate Copolymer [5] | — | — | 7.00% | — | 5.75% |
| Methacrylic acid/hydroxyethyl-methacrylate/various acrylate esters [3] | 3.00% | — | — | — | — |

TABLE 6-continued

Examples E-I Ethanol-Free Hairspray Compositions (active level %)

| | E | F | G | H | I |
|---|---|---|---|---|---|
| Polyquaternium-16 [6] | — | — | — | 2.5% | — |
| Chitosan [7] | — | — | — | 0.75% | — |
| Hydroxyethylcellulose dimethyldiallyammonium chloride[PQ4] [8] | — | — | — | — | 0.83% |
| 2-aminomethyl propanol (AMP) | — | 0.32% | — | — | — |
| Potassium Hydroxide | 0.98% | — | — | 0.40% | — |
| Fragrance | 0.10% | 0.35% | 0.18% | 0.15% | 0.2% |
| Dehyquart A-CA/Detex (cationic surfactant) | — | — | — | 0.2% | 0.2% |
| Dehydol LS 4 Deo N (Non-ionic surfactant) | — | — | 0.10% | — | 0.10% |
| PEG-12 dimethicone | — | — | — | — | — |
| Disodium EDTA | 0.11% | 0.11% | 0.11% | 0.11% | 0.11% |
| Phenoxyethanol | 0.50% | 0.50% | 0.50% | 0.50% | 0.50% |
| Methylparaben | 0.10% | 0.10% | 0.10% | 0.10% | 0.10% |
| Water | QS | QS | QS | QS | QS |

KEY:
[1] = Balance ® CR Polymer;
[2] = DynamX H20;
[3] = Acudyne 1000;
[4] = Amphomer;
[5] = Luviskol VA64;
[6] = Luviquat FC550;
[7] = Hydagen ® HCMF;
[8] = Celquat L-200.

TABLE 7

Examples J-K Ethanol-based Finishing Hairspray

| | J | JJ | K | L |
|---|---|---|---|---|
| VA/Crotoantes/Vinyl Neodecanoate Copolymer [1] | 2.16% | 3.61% | — | — |
| Octylacrylamide Acrylates Copolymer [2] | 1.94% | 3.23% | — | — |
| Octylacrylamide/ Acrylates/ Butylaminoethyl/ Methacrylate Copolymer [3] | — | — | 3.25% | 4.50% |
| Vinylpyrrolidone/ Vinylacetate Copolymer [5] | — | — | — | — |
| Water | 4.37% | 7.20% | 0.15% | 0.15% |
| 2-aminomethyl propanol (AMP) | 0.55% | 0.92% | 0.72% | 0.98% |
| Tapioca Starch | — | — | 1.50% | — |
| Silica | — | — | 0.25% | — |
| Polysorbate-80 | 0.13% | 0.22% | — | — |
| Ammonium Benzoate | 0.20% | 0.33% | — | — |
| Monoethanolamine Borate | 0.20% | 0.33% | — | — |
| Fragrance | 0.27% | 0.45% | 0.10% | 0.10% |
| Triethyl Citrate | — | — | 0.15% | — |
| Ethanol | QS | QS | QS | QS |

KEY:
[1] = Resyn 28-2930;
[2] = Amphomer;
[3] = Balance 47;

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol hairspray product comprising:
 a) a pressurizable container comprising a container wall that encloses a reservoir for storing a compressed gas propellant and a hairspray composition, wherein the hairspray composition comprises:
  i) about 60 wt % to about 98.5 wt % water,
  ii) about 1.5% to about 8% of a water-soluble hairstyling polymer that is substantially free of ethanol, isopropanol, and propanol; and
 b) a spraying device clinched onto the container for dispensing the hairspray composition from the reservoir of the container, wherein the spraying device comprises a valve assembly and a nozzle, and wherein the valve assembly comprises:
  i) a housing with internal walls defining a valve chamber comprising a liquid inlet for fluid communication with liquid in the container, and a gas inlet for fluid communication with gas in the container, and
  ii) a valve stem having a proximal end and a distal end, the proximal end received in the valve chamber and the distal end projecting through a sealed opening in the valve chamber, the valve stem comprising:
   (a) an outlet flow conduit with an outlet aperture at the distal end, and
   (b) at least one first stem inlet for liquid and at least one second stem inlet for gas,
   wherein the housing includes a lip projecting inwardly from the internal walls around at least a perimeter of the valve stem to form a seal around the perimeter of the valve stem, and the valve chamber liquid inlet is proximal of the lip and the valve chamber gas inlet is distal of the lip, and wherein the valve stem is moveable between:
   a closed position in which the at least one first stem inlet is distal of the lip and the at least one second stem inlet is distal of the sealed opening in the valve chamber such that the at least one first stem inlet is not in fluid communication with the valve chamber liquid inlet and the at least one second stem inlet is not in fluid communication with the valve chamber gas inlet, and
   an open position in which the at least one first stem inlet is proximal of the lip so as to be in fluid communication with the valve chamber liquid inlet, and the at least one second stem inlet is proximal of the sealed opening in the valve chamber and at least partially distal of the lip so as to be in fluid communication with the valve chamber gas inlet, whereby a bubble laden flow is created in the outlet flow conduit.

2. The aerosol hairspray product according to claim 1, wherein the compressed gas propellant comprises nitrogen.

3. The aerosol hairspray product according to claim 1, wherein the pressure inside the container is about 3 bar to about 5 bar, at 20° C.

4. The aerosol hairspray product according to claim 1, wherein the hairspray composition, without propellant, has a viscosity of about 0.5 cSt to about 6 cSt, at 20° C. +/−0.1° C.

5. The aerosol hairspray product according to claim 1, wherein the hairspray composition further comprises about 5.5% to about 8% of a hairstyling polymer.

6. The aerosol hairspray product according to claim 5, wherein the hairstyling polymer is an anionic hairstyling polymer selected from copolymers derived from acrylic acid, copolymers derived from crotonic acid, and mixtures thereof.

7. The aerosol hairspray product according to claim 6, wherein the copolymers derived from acrylic acid are selected from acrylic acid/ethylacrylate/n-tert-butylacrylamide terpolymers, octylacrylamide/acrylates/butylaminoethyl/methacrylate copolymers, methacrylic acid/ester acrylate/ester methacrylates copolymers, octylacrylamide/acrylates/butylaminoethyl methacrylate copolymers, methacrylic acid/hydroxyethylmethacrylate/acrylate ester copolymers, acrylates/hydroxyethylmethacrylate copolymers, methacrylic acid/hydroxyethylmethacrylate copolymers, n-butyl methacrylate/methacrylic acid/ethyl acrylate copolymers, and mixtures thereof.

8. The aerosol hairspray product according to claim 6, wherein the copolymers derived from crotonic acid are selected from vinyl acetate/vinyl tertbutylbenzoate/crotonic acid terpolymers and crotonic acid/vinyl acetate/vinyl neododecanoate terpolymers, and mixtures thereof.

9. The aerosol hairspray product according to claim 1, wherein the hairstyling polymer is selected from the group consisting of acrylates copolymers of two or more monomers of (meth) acrylic acid or an ester thereof,
octylacrylamide/acrylate/butylaminoethyl methacrylate copolymers;
acrylates/hydroxyesters acrylates copolymers, polyurethane-14/AMP-acrylates copolymer blend, and mixtures thereof.

10. A method of styling hair comprising:
applying the aerosol hairspray product of claim 1 to a target portion of hair by activating the spraying device and dispensing the hairspray composition through the nozzle at a delivery rate of about 0.3 g/sec to about 0.5 g/sec, wherein the dispensed hairspray composition comprises particles having an average particle size distribution (Dv50) of about 40 microns to about 90 microns at both the initial spray and when 25% of the hairspray composition is remaining in the container.

11. The method of claim 10, wherein the delivery rate varies by no more than 10% between the initial spray and when 25% of the hairspray composition remains in the container.

12. The method of claim 10, wherein the average particle size distribution varies by no more than 20 microns from the initial spray to when 25% of the hairspray composition is remaining in the container.

13. An aerosol hairspray product comprising:
a) a pressurizable container comprising a container wall which encloses a reservoir for storing a compressed gas propellant and a hairspray composition; wherein the hairspray composition comprises:
from about 60% to about 99% ethanol, by weight of the hairspray composition;
from about 1.5% to about 8% hairstyling polymer, by weight of the hairspray composition, wherein the hairstyling polymer is alcohol-soluble;
b) a spraying device clinched onto the container for dispensing the hairspray composition from the reservoir of the container, wherein the spraying device comprises a valve assembly and a nozzle; wherein the valve assembly comprises: a housing with internal walls defining a valve chamber, the valve chamber having a liquid inlet for fluid communication with liquid in the container, and a gas inlet for fluid communication with gas in the container; and
a valve stem having a proximal end and a distal end, the proximal end received in the valve chamber and the distal end projecting through a sealed opening in the valve chamber, the valve stem including an outlet flow conduit with an outlet aperture at the distal end and, more proximally, at least one first stem inlet for liquid and at least one second stem inlet for gas;
wherein the housing includes a lip projecting inwardly from the internal walls around at least a perimeter of the valve stem to form a seal around the entire perimeter of the valve stem, wherein the valve chamber liquid inlet is proximal of the lip and the valve chamber gas inlet is distal of the lip;
wherein the valve stem is moveable between:
a closed position in which the at least one first stem inlet is distal of the lip and the at least one second stem inlet is distal of the sealed opening in the valve chamber, such that the at least one first stem inlet is not in fluid communication with the valve chamber liquid inlet and such that the at least one second stem inlet is not in fluid communication with the valve chamber gas inlet; and
an open position in which the at least one first stem inlet is proximal of the lip so as to be in fluid communication with the valve chamber liquid inlet, and the at least one second stem inlet is proximal of the sealed opening in the valve chamber and at least partially distal of the lip so as to be in fluid communication with the valve chamber gas inlet, whereby a bubble laden flow is created in the outlet flow conduit.

14. The aerosol hairspray product according to claim 13, wherein the compressed gas propellant comprises nitrogen.

15. The aerosol hairspray product according to claim 13, wherein the hairspray composition has a viscosity of from about 3 cSt to about 18 cSt, wherein the viscosity is measured at 20° C. +/−0.1° C.

16. The aerosol hairspray product according to claim 13, wherein the hairspray composition further comprises a panthenol compound and/or a silicone compound.

17. The aerosol hairspray product according to claim 13, wherein the hairspray composition comprises from about 3% to about 7% of an anionic hairstyling polymer.

18. The aerosol hairspray product according to claim 17, wherein the anionic hairstyling polymer is selected from: copolymers derived from acrylic acid such as the acrylic acid/ethylacrylate/n-tert-butylacrylamide terpolymers; octylacrylamide/acrylates/butylaminoethyl/methacrylate copolymers; methacrylic acid/ester acrylate/ester methacrylates; octylacrylamide/acrylates/butylaminoethyl methacrylate copolymer; methacrylic acid/hydroxyethylmethacrylate/various acrylate esters; acrylates/hydroxyethylmethacrylate; methacrylic acid/hydroxyethylmethacrylate/various acrylate esters; n-butyl methacrylate/methacrylic acid/ethyl acrylate copolymers; copolymers derived from crotonic acid, such as vinyl acetate/vinyl tertbutylbenzoate/crotonic acid terpolymers; and the crotonic acid/vinyl acetate/vinyl neododecanoate terpolymers; and mixtures thereof.

19. The aerosol hairspray product according to claim 17, wherein the hairstyling polymer is selected from the group consisting of: acrylates copolymers of two or more monomers of (meth) acrylic acid or one of their simple esters;

octylacrylamide/acrylate/butylaminoethyl methacrylate copolymers;

acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof.

\* \* \* \* \*